US006486382B1

(12) United States Patent
Gordan-Kamm et al.

(10) Patent No.: US 6,486,382 B1
(45) Date of Patent: Nov. 26, 2002

(54) USE OF THE GREEN FLUORESCENT PROTEIN AS A SCREENABLE MARKER FOR PLANT TRANSFORMATION

(75) Inventors: William Gordan-Kamm, Urbandale, IA (US); Dorothy A. Pierce, Urbandale, IA (US); Benjamin Bowen, Des Moines, IA (US); Dennis Bidney, Urbandale, IA (US); Margit Ross, Johnston, IA (US); Christopher Scelonge, Des Moines, IA (US); Michael D. Miller, Winterset, IA (US); Gary Sandahl, West Des Moines, IA (US); Lijuan Wang, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/214,909

(22) PCT Filed: May 1, 1997

(86) PCT No.: PCT/US97/07688

§ 371 (c)(1),
(2), (4) Date: Dec. 20, 1999

(87) PCT Pub. No.: WO97/41228

PCT Pub. Date: Nov. 6, 1997

Related U.S. Application Data

(60) Provisional application No. 60/016,345, filed on May 1, 1996.

(51) Int. Cl.[7] .................... C12N 15/82; C12N 15/90; C12N 5/04; A01H 5/00; A01H 5/10
(52) U.S. Cl. ................ 800/278; 435/69.8; 435/320.1; 435/419; 536/23.6; 800/287; 800/298; 800/306; 800/320.1
(58) Field of Search .................... 435/69.1, 320.1, 435/69.8, 410, 412, 419, 468; 536/23.6; 800/278, 288, 287, 295, 298, 306, 320.1

(56) References Cited

U.S. PATENT DOCUMENTS

| 5,162,227 A | 11/1992 | Cormier .................. 435/320.1 |
| 5,360,728 A | 11/1994 | Prasher ....................... 435/189 |
| 5,422,266 A | 6/1995 | Cormier et al. ............. 435/471 |
| 5,491,084 A | 2/1996 | Chalfie et al. ............... 435/189 |
| 6,146,826 A | 11/2000 | Chalfie et al. .................. 435/6 |

FOREIGN PATENT DOCUMENTS

| EP | 0 540 064 A1 | 5/1993 | ............ C12N/15/12 |
| WO | WO 92/01370 | 2/1992 | ............ A01H/5/00 |
| WO | WO 93/01283 | 1/1993 | ............ C12N/15/00 |
| WO | WO 94/03619 | 2/1994 | ............ C12N/15/82 |
| WO | WO 94/17176 | 8/1994 | ............ C12N/5/00 |
| WO | WO 95/07463 | 3/1995 | .......... G01N/33/53 |
| WO | WO 95/21191 | 8/1995 | ......... C07K/14/435 |
| WO | WO 96/27675 | 9/1996 | ............ C12N/15/82 |

OTHER PUBLICATIONS

Delagrave et al., "Red-Shifted Excitation Mutants of the Green Fluorescent Protein", *Bio/Technology* 13:151–154 (1995).
Hassler, Susan, "Green Fluorescent Protein: The Next Generation", *Bio/Technology* 13:103 (1995).
Kain et al., "Green Fluorescent Protein as a Reporter of Gene Expression and Protein Localization", *BioTechniques* 19(4):655 (1995).
Horsch et al., "Inheritance of Functional Foreign Genes in Plants", Science 233:496–498 (1984).
Prasher et al., "Primary structure of the *Aequorea victoria* green-fluorescent protein" *Gene* 111:229–233 (1992).
Valvekens et al., "*Agrobacterium tumefaciens*–mediated transformation of *Arabidopsis thaliana* root explants by using kanamycin selection", *Proc. Natl. Acad. Sci. USA* 85:5536–5540 (1988).
Jurgen Haas et al., "Codon Usage Limitation in the Expression of HIV–1 Envelope Glycoprotein," *Current Biology* 1996, vol. 6 No. 3:315–324.
Chalfie et al. Science, 263: 802, 805 (1994).
Balzan et al. Proc. Nat Acad. Sci. 92: 4219–4223 (1995).
Conklin et al. Plant Physiol. 109 203–212 (1995).
Chiu, et al., "Engineered GFP as vital reporter in plants", *Curr. Biol.* 6(3): 325—330 (1996).

(List continued on next page.)

*Primary Examiner*—Amy J. Nelson
*Assistant Examiner*—Ashwin Mehta
(74) *Attorney, Agent, or Firm*—Pioneer Hi-Bred International, Inc.

(57) ABSTRACT

A method for the production of transgenic plants is provided in which a vector carrying a gene encoding the green fluorescent protein is introduced into cells, the cells are screened for the protein and transformed cells are selected and regenerated. The cellular toxicity of the green fluorescent protein is circumvented by regulating expression of the gene encoding the protein or directing the protein to a subcellular compartment where it is not toxic to the cell. DNA constructs are provided for cell transformation in which the expression of a gene encoding the green fluorescent protein is placed under the control of an inducible promoter. In addition, DNA constructs are provided in which a nucleotide sequence encoding the green fluorescent protein is operably linked to a signal sequence which directs the expressed protein to a subcellular compartment where the protein is not toxic to the cell. Oxidative stress to plant cells transformed with GFP also can be ameliorated by transforming cells with an expression vector comprising genes encoding GFP and an oxygen scavenger enzyme such as superoxide dismutase. The toxicity of GFP in transformed plants can be eliminated by excising the screenable marker gene following detection of transformed cells or sectors. The FLP/FRT system is used in conjunction with GFP as a visible marker for transformation and FRT excision. A nucleotide sequence optimized for expression of the green fluorecent protein in plants is also provided.

33 Claims, 6 Drawing Sheets

OTHER PUBLICATIONS

Sheen, et al., "Green–fluorescent protein as a new vital marker in plant cells", *The Plant Journal* 8(5): 777–784 (1995).

Haas, et al., "Cloning vector phGFP–S65T, complete sequence, green fluorescent protein (gfp) gene, complete cds", EMBL *Sequence Database Rel*. 46 U43284: 829–1545 (Jan. 24, 1996).

Haseloff, et al., "GFP in plants", TIC 11(8): 328–329 (Aug. 1995).

Heinlein, et al., "Interaction of Tobamovirus Movement Protein with the Plant Cytoskeleton", Science 270: 1983–1985 (Dec. 22, 1995).

Haseloff, et al., "Removal of a cryptic intron and subcellular localizaton of green fluorescent protein are required to mark transgenic *Arabidopsis* plants brightly", *Proc. Natl. Acad. Sci.* USA 94: 2122–2127 (Mar. 1997).

Pang, et al., "An Improved Green Fluorescent Protein Gene as a Vital Marker in Plants", *Plant Physiol.* 112: 893–900 (1996).

Yoder, et al., "Transformation Systems for Generating Marker–Free Transgenic Plants", *Biotechnology* 12(3): 263–267 (Mar. 1994).

Dale, et al., "Gene transfer with subsequent removal of the selection gene from the host genome", *Proc. Natl. Acad. Sci.* USA 88: 10558–10562 (Dec. 1991).

Goldsbrough, et al., "Transposition Mediated Re–positioning and Subsequent Elimination of Marker Genes from Transgenic Tomato", Biotechnology 11: 1286–1291 (Nov. 11, 1993).

Lloyd, et al., "Functional expression of the yeast FLP/FRT site–specific recombination system in *Nicotiana tabacum*", *Mol. Gen. Genet.* 242: 653–657 (1994).

Gleave, "A versatile binary vector system with a T–DNA organisational structure conductive to efficient integration of a cloned DNA into the plant genome", Plant Molecular Biology 20: 1203–1207 (1992).

FIG. 1A

```
      ATGTCCAAGGGCGAGGAGCTCTTCACCGGCGTGGTGCCCATCCTCGTGGAGCTCGACGGC
  1   ------+---------+---------+---------+---------+---------+     60
      TACAGGTTCCCGCTCCTCGAGAAGTGGCCGCACCACGGGTAGGAGCACCTCGAGCTGCCG

M   S   K   G   E   E   L   F   T   G   V   V   P   I   L   V   E   L   D   G

GACGTGAACGGCCACAAGTTCTCCGTGTCCGGCGAGGGCGAGGGCGACGCCACCTACGGC
 61   ------+---------+---------+---------+---------+---------+    120
      CTGCACTTGCCGGTGTTCAAGAGGCACAGGCCGCTCCCGCTCCCGCTGCGGTGGATGCCG

D   V   N   G   H   K   F   S   V   S   G   E   G   E   G   D   A   T   Y   G

AAGCTCACCCTCAAGTTCATCTGCACCACCGGCAAGCTCCCCGTGCCCTGGCCCACCCTC
121   ------+---------+---------+---------+---------+---------+    180
      TTCGAGTGGGAGTTCAAGTAGACGTGGTGGCCGTTCGAGGGGCACGGGACCGGGTGGGAG

K   L   T   L   K   F   I   C   T   T   G   K   L   P   V   P   W   P   T   L

GTGACCACCTTCTCCTACGGCGTGCAGTGCTTCTCCAGTACCCCGACCACATGAAGCAG
181   ------+---------+---------+---------+---------+---------+    240
      CACTGGTGGAAGAGGATGCCGCACGTCACGAAGAGGTCCATGGGGCTGGTGTACTTCGTC

V   T   T   F   S   Y   G   V   Q   C   F   S   R   Y   P   D   H   M   K   Q

CACGACTTCTTCAAGTCAGCCATGCCCGAGGGCTACGTGCAGGAGAGGACCATCTTCTTC
241   ------+---------+---------+---------+---------+---------+    300
      GTGCTGAAGAAGTTCAGTCGGTACGGGCTCCCGATGCACGTCCTCTCCTGGTAGAAGAAG

H   D   F   F   K   S   A   M   P   E   G   Y   V   Q   E   R   T   I   F   F

AAGGACGACGGCAACTACAAGACCAGGGCCGAGGTGAAGTTCGAAGGCGACACCCTCGTG
301   ------+---------+---------+---------+---------+---------+    360
      TTCCTGCTGCCGTTGATGTTCTGGTCCCGGCTCCACTTCAAGCTTCCGCTGTGGGAGCAC

```
361  AACAGGATTGAGCTCAAGGGCATCGACTTCAAGGAGGACGGCAACATCCTCGGCCACAAG
     ------+---------+---------+---------+---------+---------+  420
     TTGTCCTAACTCGAGTTCCCGTAGCTGAAGTTCCTCCTGCCGTTGTAGGAGCCGGTGTTC
      N  R  I  E  L  K  G  I  D  F  K  E  D  G  N  I  L  G  H  K

421  CTCGAGTACAACTACAACTCCCACAACGTGTACATCATGGCCGACAAGCAGAAGAACGGC
     ------+---------+---------+---------+---------+---------+  480
     GAGCTCATGTTGATGTTGAGGGTGTTGCACATGTAGTACCGGCTGTTCGTCTTCTTGCCG
      L  E  Y  N  Y  N  S  H  N  V  Y  I  M  A  D  K  Q  K  N  G

481  ATCAAGGTGAACTTCAAGATCAGGCACAACATCGAGGACGGCTCAGTGCAGCTCGCTGAC
     ------+---------+---------+---------+---------+---------+  540
     TAGTTCCACTTGAAGTTCTAGTCCGTGTTGTAGCTCCTGCCGAGTCACGTCGAGCGACTG
      I  K  V  N  F  K  I  R  H  N  I  E  D  G  S  V  Q  L  A  D

541  CACTACCAGCAGAACACCCCCATCGGCGACGGCCCCGTGCTCCTCCCCGACAACCACTAC
     ------+---------+---------+---------+---------+---------+  600
     GTGATGGTCGTCTTGTGGGGGTAGCCGCTGCCGGGGCACGAGGAGGGGCTGTTGGTGATG
      H  Y  Q  Q  N  T  P  I  G  D  G  P  V  L  L  P  D  N  H  Y

601  CTCTCCACCCAGTCCGCCCTCTCCAAGGACCCCAACGAGAAGAGAGGACCACATGGTGCTC
     ------+---------+---------+---------+---------+---------+  660
     GAGAGGTGGGTCAGGCGGGAGAGGTTCCTGGGGTTGCTCTTCTCCTGGTGTACCACGAG
      L  S  T  Q  S  A  L  S  K  D  P  N  E  K  R  D  H  M  V  L

661  CTCGAGTTCGTGACCGGCTGCTGGCATCACCCACGGGCATGGACGAGCTCTACAAGTGA
     ------+---------+---------+---------+---------+---------+  717
     GAGCTCAAGCACTGGCCGACGACCGTAGTGGGTGCCCGTACCTGCTCGAGATGTTCACT
      L  E  F  V  T  A  A  G  I  T  H  G  M  D  E  L  Y  K  *
```

USE OF THE GREEN FLUORESCENT PROTEIN AS A SCREENABLE MARKER FOR PLANT TRANSFORMATION

This application is a United States national stage entry of PCT International Application No. PCT/US/07688, filed May 1, 1997, which claims the benefit of provisional U.S. Application No. 60/016,345, filed May 1, 1996.

BACKGROUND OF THE INVENTION

1. Field of the Invention

The present invention relates to a method of plant transformation in which a DNA construct carrying a gene encoding the green fluorescent protein (GFP) is introduced into plant cells which are then screened for the presence of the protein and transformed cells are regenerated into transgenic plants. In particular, the present invention provides methods for circumventing the cellular toxicity of the GFP by regulating expression of the gene encoding the protein or directing the protein to a subcellular compartment where it is not toxic to the cell. The present invention provides DNA constructs for cell transformation in which expression of a gene encoding the GFP is placed under the control of an inducible, constitutive or tissue-specific promoter. In addition, DNA constructs are provided in which a nucleotide sequence encoding the GFP is operably linked to a signal or targeting sequence which directs the expressed protein to a subcellular compartment where the protein is not toxic to the cell. Moreover, the present invention provides a nucleotide sequence encoding GFP that is optimized for expression of the GFP gene in plants and to GFP-encoding nucleotide sequences that code for light-shifted versions of GFP. The present invention also provides a method for selecting plant cells transformed with a gene encoding a screenable marker flanked on the 5-prime and 3-prime ends with a recombinase-specific target sequence, and introducing a gene encoding a site specific recombinase into the transformed plant cells and selecting transformed plant cells that no longer express the screenable marker. In addition, the present invention provides a method of reducing GFP toxicity by transforming plant cells with a gene encoding the GFP together with a gene encoding an oxygen scavenger such as superoxidase dismutase.

2. Background

Expression vectors include at least one genetic marker that allows transformed cells to be either recovered by negative selection, i.e. inhibiting growth of cells that do not contain the selectable marker gene, or by screening for product encoded by the genetic marker. Many of the commonly used selectable marker genes for plant transformation were isolated from bacteria and code for enzymes that metabolically detoxify a selective chemical agent which may be an antibiotic or a herbicide. Other selectable marker genes encode an altered target which is insensitive to the inhibitor.

The most commonly used selectable marker gene for plant transformation is the neomycin phosphotransferase II (nptII) gene, isolated from Tn5, which when placed under the control of plant regulatory signals confers resistance to kanamycin. Fraley et al., *Proc. Natl. Acad. Sci. U.S.A.,* 80: 4803 (1983). Another commonly used selectable marker gene is the hygromycin phosphotransferase gene which confers resistance to the antibiotic hygromycin. Vanden Elzen et al., *Plant Mol. Biol.,* 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.,* 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or broxynil. Comai et al., *Nature* 317: 741–744 (1985), Gordon-Kamm et al., *Plant Cell* 2: 603–618 (1990) and Stalker et al., *Science* 242: 419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Although many of these markers have been used for selecting transformed plant tissue, these selection systems involving toxic chemical agents can have disadvantages or limitations. One disadvantage is that it may be difficult to recover normal, viable transformed plants directly from chemical selection. Everett et al., *Bio/Technology* 5: 1201–1204 (1987). Another disadvantage is that not all selectable marker systems work for all tissues, in all plant species, due in part to differences in sensitivity of a particular tissue or plant species to the selective agent. The success of any given marker for transformation of a given plant species is not easily predicted. Moreover, potential regulatory issues surrounding the use of antibiotic resistance genes and the use of herbicide resistance genes for plant species capable of outcrossing with weedy species are additional disadvantages of these markers.

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84: 131 (1987), De Block et al., *EMBO J.* 3: 1681 (1984). Another approach to the identification of relatively rare transformation events has been use of a gene that encodes a dominant constitutive regulator of the *Zea mays* anthocyanin pigmentation pathway. Ludwig et al., *Science* 247: 449 (1990).

Although chemical selection of plant cells transformed with selectable marker genes has been successful with plant species and varieties that are easily cultured in vitro, the choice of selectable marker systems that have been shown to be successful for cereals and many other agronomically important plant species is very limited. In general, plant species that tend toward organogenesis and/or shoot propagation have been difficult to transform by means of chemical selection. The success rate with these plant species continues to improve, however, as evidenced by recent advances in Type I selection of maize inbreds and small grain cereals such as barley. Koziel et al., *Bio/Technology* 11: 194–200 (1993) and Mendel et al. In: *Transformation of Plants and Soil Microorganisms,* Wang et al. eds., Cambridge Press (1995).

Likewise, there has been little success in using visual screening methods for primary identification of transformed cells. The GUS gene was used to investigate germline transmission. McCabe et al., *Plant Physiol.*, 87(3): 671 (1988) and McCabe et al., *Plant Cell Tissue Organ Cult.* 33 (3): 227 (1993). Histochemical staining for GUS activity was used to locate transgenic sectors in cotton and soybean transformants that ultimately produced transgenic seeds. Since histochemical analysis for GUS activity requires destruction of portions of the presumptively transformed plant tissue, this method is labor intensive and impractical for routine production of transgenic plants. This method is particularly unsuitable for plant species such as maize and other cereals in which transformants are recovered, even under optimum conditions, at low frequency. Recovery of transformed progeny was reported once in barley using GUS expression as a screening tool, but the method was found to be very labor-intensive. Ritala et al., *Plant Mol. Biol.* 24: 317–325 (1994). There have been no reports at all of success with GUS or other screenable markers with maize.

More recently, in vivo methods for visualizing GUS activity that do not require destruction of plant tissue have been made available. Molecular Probes Publication 2908, Imagene Green™, p. 1–4 (1993) and Naleway et al., *J. Cell Biol.* 115: 151a (1991). However, these in vivo methods for visualizing GUS activity have not proven useful for recovery of transformed cells because of low sensitivity and high fluorescent backgrounds.

Despite the fact that luciferase genes have been available for many years, this strategy for visualizing transformed cells has also not been successfully adapted for routine recovery of plant transformants. The luciferase-based screening methods are limited by the fact that most of these systems require the presence of luciferin, a compatible luciferase and an exogenously supplied cofactor. In the absence of the substrate, enzyme or cofactor, the system does not bioluminesce. Cells transformed with a luciferase gene must have cell walls and plasma membranes that are permeable, or rendered permeable, to a compatible luciferin in order to detect bioluminescence. For example, tobacco plants regenerated from cells transformed with a firefly luciferase gene and exposed to a liquid medium containing firefly luciferin exhibited bioluminescence primarily along their major veins. Ow et al., *Science* 234: 856 (1986). Accordingly, a screening method has not been successfully developed for routine plant transformation that does not involve chemical selection or assays, often labor-intensive, that require the sacrifice or destruction of tissue samples for analysis.

A gene encoding GFP has been utilized as a marker for gene expression in prokaryotic and eukaryotic cells. Chalfie et al., *Science* 263: 802 (1994). Many cnidarians utilize GFPs as energy-transfer acceptors in bioluminescence. A gene encoding GFP isolated from a cnidarian and expressed in a heterologous prokaryotic or eukaryotic host produces a protein capable of fluorescence. A cDNA encoding the Aequorea victoria GFP produced a fluorescent product when expressed in *Escherichia coli* or *Caenorhabditis elegans* cells. Green fluorescence was detected in transformed cells upon illumination with a long-wave ultraviolet (UV) source without having to supply substrates or cofactors. In addition, fluorescence was stable for at least 10 min when illuminated with 450 to 490 nm light. Transformation of plant cells with a gene encoding GFP and detection of fluorescence has been reported. Haseloff et al., *TIG* 11: 328–329 (1995). Transformed Arabidopsis cells could be regenerated into whole plants. However, the regenerated plants expressing GFP exhibited signs of mild to moderate toxicity in the light compared to plants not expressing GFP. The strongest GFP expressors proved more difficult to regenerate. Likewise, in a recent report describing GFP expression in kanamycin-selected tobacco transformants, Chiu et al., *Current Biol.* 6: 325–330 (1996) note that high GFP expression levels inhibited regeneration of transgenic plants.

A need therefore exists for a cell transformation method which does not rely, or does not rely solely on, selection of cells carrying a gene that confers resistance to a toxic substance. A need exists for a method for efficiently and easily identifying transformed plant cells with a visual screenable marker. A need also exists for a method of cell transformation that does not require destruction of presumptively transformed tissue to assay for the presence of a selectable marker gene. A need exists for a method for cell transformation that combines a selectable marker gene and a screenable marker gene. In addition, a need exists for a method of cell transformation which does not require exogenous supply of a substrate or cofactor for detection of the polypeptide encoded by a selectable marker gene. Yet another need exists for a method of cell transformation that circumvents the cellular toxicity of the GFP.

SUMMARY OF THE INVENTION

Accordingly, it is an object of the present invention to provide a method for cell transformation which does not depend on selection of cells carrying a gene that confers resistance to a toxic substance.

It is another object of the present invention to provide a method for cell transformation which combines the selection of cells carrying a gene that confers resistance to a toxic substance with screening cells for the presence of a substance that renders transformed cells identifiable.

It is a further object of the present invention to provide a method for cell transformation which does not require destruction of presumptively transformed tissue to assay for the presence of a selectable marker gene.

Yet another object of the present invention is to provide a method for cell transformation which does not require that an exogenous substrate or cofactor be provided to assay for a polypeptide encoded by a selectable marker gene.

It is another object of the present invention to provide a method for cell transformation that circumvents the cellular toxicity of the GFP.

These and other objects are achieved, in accordance with one embodiment of the present invention, by providing an isolated DNA molecule comprising a nucleotide sequence encoding the GFP operably linked to an inducible promoter. The inducible promoter can be selected from the group consisting of the estrogen-inducible promoter, the estradiol-inducible promoter, the ACE1 promoter, the IN2 promoter and the tetracycline repressor promoter.

Also provided is an isolated DNA molecule comprising as nucleotide sequence encoding the GFP wherein the nucleotide sequence is operably linked to a targeting sequence for subcellular localization which directs a protein to a subcellular compartment.

An isolated DNA molecule is provided comprising a nucleotide sequence selected from the group consisting of (a) SEQ ID NO: 1; (b) a nucleotide sequence that has substantial sequence similarity with SEQ ID NO: 1; and (c) a functional fragment of (a) or (b), wherein said DNA molecule encodes a GFP. The nucleotide sequence encoding a GFP may be operably linked to a nucleotide sequence encoding a targeting sequence for subcellular localization which directs a protein to a subcellular compartment. The nucleotide sequence encoding a GFP and a targeting sequence may further comprise a promoter operably linked to said nucleotide sequence.

Also provided are expression vectors comprising DNA molecules encoding a GFP, optionally operably linked to an inducible promoter and/or targeting sequence. The expression vector of the instant invention may carry a nucleotide sequence encoding a foreign protein operably linked to a second promoter.

Also provided is a method of using the expression vectors of the instant invention to produce a transformed plant, comprising the steps of introducing an expression carrying a gene encoding GFP into regenerable plant cells and selecting cells containing the GFP for regeneration. The method of the instant invention may include the step of inducing GFP expression where the nucleotide sequence encoding GFP is operably linked to an inducible promoter. The regenerable plant cells utilized in the method of the instant invention are selected from the group consisting of Zea, Brassica and Helianthus cells.

Also provided are transgenic plants expressing the isolated DNA molecule encoding GFP. In addition, transgenic plants comprising a vector carrying a nucleotide sequence encoding GFP are provided.

A method for producing a transgenic plant is provided comprising the steps of (a) constructing an expression vector comprising (i) a first promoter which is an inducible promoter, operably linked to a nucleotide sequence encoding a GFP, and (ii) a second promoter operably linked to a foreign gene; (b) introducing said expression vector into regenerable plant cells; (c) inducing expression of the gene encoding the GFP and selecting transformed plant cells containing said protein; and (d) regenerating transformed plants from said selected transformed plant cells. The inducible promoter may be selected from the group including the estrogen-inducible promoter, the estradiol-inducible promoter, the ACEI promoter, the IN2 promoter and the tetracycline repressor promoter.

Also provided is a method for producing a transgenic plant, comprising the steps: (a) constructing an expression vector comprising (i) a first promoter operably linked to a nucleotide sequence encoding a sequence for subcellular localization which directs a protein to a subcellular compartment which is operably linked to a nucleotide sequence encoding a GFP, and (ii) a second promoter operably linked to a foreign gene; (b) introducing said expression vector into regenerable plant cells; (c) selecting transformed plant cells containing said GFP; and (d) regenerating transformed plants from said selected transformed plant cells. The targeting sequence for subcellular localization directs the GFP to the mitochondria, chloroplasts, peroxisomes, vacuole, endoplasmic reticulum. cell wall or for secretion generally into the apoplast. This method may include a nucleotide sequence encoding a GFP selected from the group consisting of: (a) SEQ ID NO: 1; (b) a nucleotide sequence that has substantial sequence similarity with SEQ ID NO: 1; and (c) a functional fragment of (a) or (b).

Also provided is a method for producing a transgenic plant, comprising the steps: (a) constructing an expression vector comprising (i) a first promoter operably linked to a nucleotide sequence encoding a screenable marker flanked on the 5-prime and 3-prime ends with a recombinase-specific target sequence, and (ii) a second promoter operably linked to a foreign gene; (b) introducing said expression vector into regenerable plant cells; (c) selecting transformed plant cells containing said screenable marker; (d) transforming the plant cells with a second expression vector containing a gene encoding a site-specific recombinase; (e) selecting plant cells that no longer express the screenable marker; (f) regenerating transformed plants from said selected transformed plant cells; and (g) isolating said foreign protein. The site-specific recombinase may be selected from the group consisting of the FLPtFRT, Ac/DS and cre/lox systems. In addition, the screenable marker may be the GFP.

An isolated DNA molecule comprising a nucleotide sequence encoding the GFP fused in frame to a nucleotide sequence encoding superoxide dismutase is also provided. Cells transformed with the DNA molecule contain a fusion protein that (i) produces green fluorescence in the presence of UV to blue light and (ii) displays superoxide dismutase activity.

Also provided is a method for producing a transgenic plant comprising: (a) constructing an expression vector comprising (i) a first promoter operably linked to a nucleotide sequence encoding a GFP, and (ii) a second promoter operably linked to a gene encoding an enzyme that is an oxygen scavenger, and (iii) a third promoter operably linked to a foreign gene; (b) introducing said expression vector into regenerable plant cells; (c) selecting transformed plant cells containing said GFP; and (d) regenerating transformed plants from said selected transformed plant cells. The oxygen scavenger enzyme may be superoxide dismutase.

Alternatively, a method for producing a transgenic plant is provided comprising: (a) constructing an expression vector comprising (i) a first promoter operably linked to a nucleotide sequence encoding a fusion protein comprising the GFP and an oxygen scavenger enzyme fused in frame, and (ii) a second promoter operably linked to a foreign gene; (b) introducing said expression vector into regenerable plant cells; (c) selecting transformed plant cells containing said the GFP and oxygen scavenger enzyme activity; and (d) regenerating transformed plants from said selected transformed plant cells. The oxygen scavenger enzyme may be superoxide dismutase.

BRIEF DESCRIPTION OF THE DRAWINGS

FIGS. 1A–B presents the nucleotide sequence [SEQ ID NO: 1] encoding a GFP with its corresponding amino acid sequence [SEQ ID NO: 2].

DETAILED DESCRIPTION

1. Definitions

Figure 2:
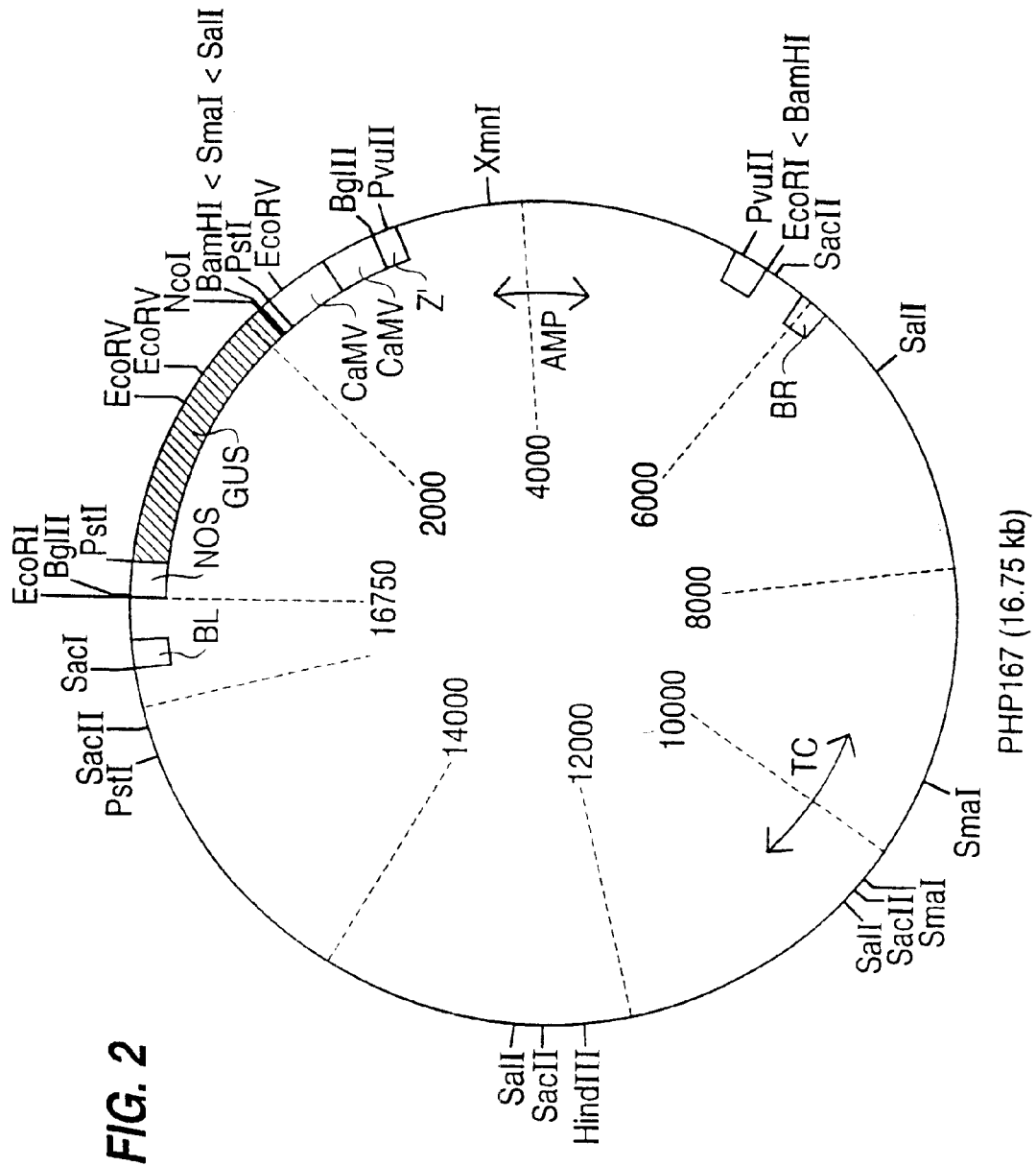
FIG. 2 shows the Plasmid Map of PHP167.
Figure 3:
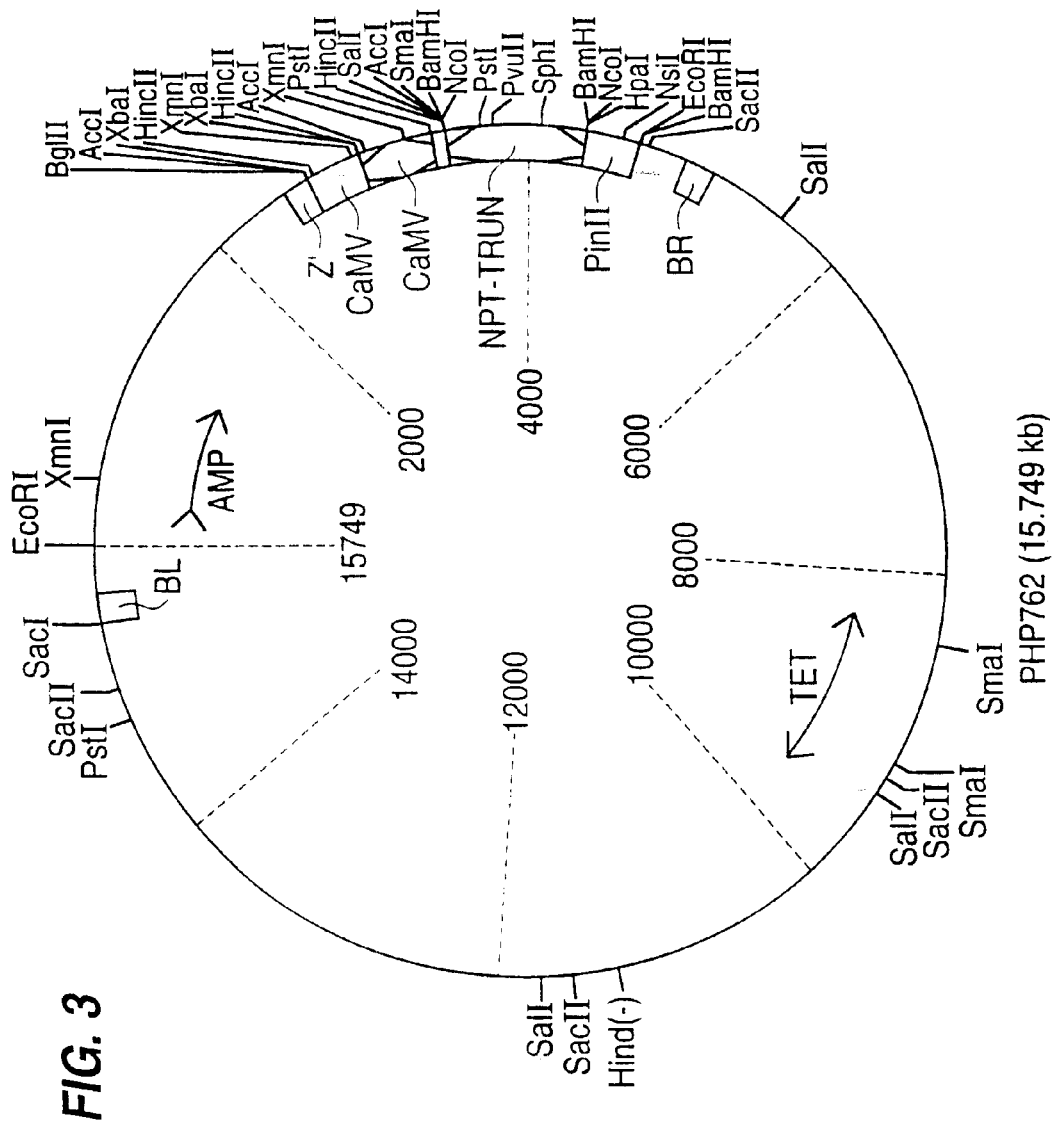
FIG. 3 shows the Plasmid Map of PHP762.

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5-prime region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. For example, a promoter may be regulated in a tissue-specific or tissue-preferred manner such that it is only active in transcribing the associated coding region in a specific tissue type(s) such as leaves, roots or meristem.

A cytotlasmically localized protein is a protein coded for by a gene which does not include any specific signal for targeting of the protein into any subcellular organelle or compartment or any signals for secretion of the protein. For example, the GFP structural gene operably linked 5-prime to a promoter and to an appropriate 3-prime sequence encodes for a protein compartmentalized in the cytoplasm.

A signal or targeting sequence is a structural peptide domain required for targeting of a given polypeptide to a subcellular organelle, subcellular compartment or secretion from the cell. As used herein, the phrase sequence for subcellular localization is intended to refer collectively to any form of signal, targeting or retention sequence as defined herein. Signal sequences for a polypeptide directed to the chloroplast or mitochondrion are largely localized to the amino-terminus of the polypeptide. Signal sequences for a polypeptide directed to the glyoxysomes and peroxisomes are largely localized to the carboxy-terminal domains of the polypeptide. Accordingly, targeted transport of the GFP protein is accomplished by means of chemically joining in proper reading frame, or operably linking, the nucleotide sequence encoding a signal sequence to the 5-prime and/or 3-prime region of the GFP structural gene.

A mitochondrial targeting sequence facilitates the transport of a protein to a mitochondrial compartment.

Typically, the mitochondrial targeting sequence is located at the amino-terminus of a polypeptide.

A secretion targeting sequence targets a polypeptide for export into the extracellular space through the ER. For example, operably linking a nucleotide sequence encoding the barley alpha amylase 1 (BAA) secretory targeting sequence to the 5-prime end of a structural gene targets the encoded protein for export into the extracellular space.

A cell wall targeting sequence targets a polypeptide for export from the cell but the polypeptide is specifically localized to the cell wall. For example, cell wall localization of a polypeptide is accomplished by operably linking a nucleotide sequence encoding BAA 5-prime, and operably linking a nucleotide sequence encoding a portion of the maize hydroxyproline-rich glycoprotein 3-prime to a gene encoding the polypeptide. Steifel et al., *Plant Cell* 2: 785–793 (1990).

A vacuolar signal sequence facilitates the transport of a protein to the vacuole. For example, vacuolar targeting is accomplished by fusing the BAA secretory signal sequence at the amino-terminus of the protein and a sequence encoding a vacuolar signal sequence to the carboxy-terminus. Transport of a polypeptide to the vacuole is therefore accomplished by means operably linking a nucleotide sequence encoding BAA 5-prime, and a nucleotide sequence encoding a vacuolar signal sequence 3-prime to a gene encoding a polypeptide. Alternatively, vacuolar targeting is accomplished by constructing a nucleotide sequence comprising in the 5-prime to 3-prime direction nucleotide sequences encoding a vacuole signal sequence, BAA and a polypeptide.

An endoplasmic reticulum retention sequence targets a polypeptide for localization in the lumen of the endoplasmic reticulum. For example, a polypeptide is targeted for retention in the endoplasmic reticulum through the addition of the BAA sequence on the amino-terminus and an endoplasmic reticulum signal sequence on the carboxy-terminus of the polypeptide.

A nuclear targeting sequence facilitates transport of a polypeptide to the nucleus. Typically, the nuclear signal sequence is located at the amino-terminus of a polypeptide. In order to retain the nuclear targeted protein in the nucleus, it may be necessary to increase the molecular weight of the protein by means of fusing an unrelated protein to the carboxy-terminus-of the targeted protein. For example, GFP was retained in the nucleus by operably linking a nucleotide sequence encoding a nuclear signal sequence 5-prime and a nucleotide sequence encoding maize acetolactate synthase 3-prime to a gene encoding a polypeptide.

A peroxisomal targeting sequence facilitates the transport of a polypeptide into the peroxisome. Typically, the peroxisomal signal sequence is a tripeptide located at the carboxy-terminus of a polypeptide.

A chloroplast targeting sequence facilitates the transport of a nuclear encoded protein to a chloroplast compartment. Typically, the chloroplast signal sequence is located at the amino-terminus of a polypeptide. Accordingly, transport of a polypeptide to a chloroplast compartment is accomplished by means of operably linking the nucleotide sequence encoding a chloroplast signal sequence to the 5-prime region of a gene encoding a polypeptide.

An isolated DNA molecule is a fragment of DNA that is not integrated in the genomic DNA of an organism.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include, for example, genes that provide tetracycline resistance, ampicillin resistance or kanamycin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be operably linked to the regulatory elements.

Transformation includes introduction of genetic material into plant cells resulting in chromosomal integration and stable heritability through meiosis. Transformation also includes introduction of genetic material into plant cells in the form of plant viral vectors involving epichromosomal replication and gene expression which may exhibit variable properties with respect to meiotic stability.

A foreign gene refers in the present description to a DNA sequence that is operably linked to at least one heterologous regulatory element.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain an expression vector.

A green fluorescent protein (GFP), or a functional fragment of a GFP, is capable of producing a green fluorescence. GFP absorbs in the UV to blue range with a peak at 395 nm and emits in the green with a peak at 510 nm. The "red-shifted" version of GFP is a modified version of GFP which absorbs between 480 to 490 nm and emits in the green with a peak at 510 nm. Red-shifted GFP is abbreviated as GFPr. The "blue fluorescent protein" is a modified version of GFP which absorbs around 380 nm and emits in the blue with a peak at around 445 nm. Blue fluorescent protein is abbreviated as BFP. $GFP_m$ is a nucleotide sequence coding for GFP in which the DNA sequence has been modified based on codon preference in maize (FIG. 1).

Two nucleic acid molecules are considered to have a substantial sequence similarity if their nucleotide sequences share a similarity of at least 50%. Sequence similarity determinations can be performed, for example, using the FASTA program (Genetics Computer Group; Madison, Wis.). Alternatively, sequence similarity determinations can be performed using BLAST (Basic Local Alignment Search Tool) of the Experimental GENIFO(R) BLAST Network Service. See Altschul et al., *J. Mol. Biol.* 215: 403 (1990). Also, see Pasternak et al., "Sequence Similarity Searches, Multiple Sequence Alignments, and Molecular Tree Building," in METHODS IN PLANT MOLECULAR BIOLOGY AND BIOTECHNOLOGY, Glick et al. (eds.), pages 251–267 (CRC Press 1993).

2. Reducing GFP Toxicity in Transformed Plants

Oxidative stress associated with GFP fluorescence has been suggested to cause cellular toxicity. Haseloff et al., *TIG* 11: 328–329 (1995). If GFP is to be useful as a screenable marker for plant transformation, as well as a reporter gene for detection of gene expression, strategies for reducing GFP toxicity must be available. The gene encoding GFP can be operably linked to an inducible promoter so that GFP can be transiently expressed and transformed cells identified. Alternatively, the gene encoding GFP can be operably linked to a signal sequence for targeting to an organelle or subcellular compartment or for secretion to the apoplast where GFP is not toxic to the cell.

Oxidative stress can be ameliorated by transforming cells containing GFP with an enzyme that serves as an oxygen scavenger. Such enzymes are well known in the art. For example, genes encoding the enzyme superoxide dismutase may protect against the primary oxidative stresses associated with GFP fluorescence. Balzan et al., *Proc. Nat Acad. Sci.* 92: 4219–4223 (1995). Other enzymes involved in the oxidative stress response, such as ascorbate peroxidase or glutathione S-transferase, could help mitigate secondary effects in the cell. Conklin, *Plant Physiol.* 109: 203–212 (1995).

More specifically, oxidative stress can be ameliorated by transforming cells with a DNA construct carrying genes encoding GFP and SOD. Alternatively, the gene encoding GFP can be fused in frame to the gene encoding SOD. Cells transformed with this DNA construct produce a fusion protein that cause the cells to fluoresce in the presence of UV-blue light and express SOD activity.

The toxicity of GFP in transformed plants can be eliminated by excising the screenable marker gene following detection of transformed cells or sectors. The FLP/FRT system is used in conjunction with GFPm as a visible viable marker for FRT excision. The FLP/FRT system has been demonstrated in maize suspension cells using GUS expression as an indicator of FRT excision. Lysnik et al., *NAR* 21: 969–975 (1993). For example, plant cells are bombarded with a DNA construct containing the GFP gene flanked by FRT sequences as well as a foreign or agronomic gene of interest. The GFP gene may be operably linked to a constitutive promoter or an inducible promoter. In addition, the GFP gene may be operably linked to a signal sequence. Stable transformants are detected by means of screening for GFP.

Transgenic callus pieces are spread on medium and bombarded a second time with a FLP recombinase construct. Callus is monitored periodically under UV to blue illumination to detect cells that no longer express GFP. Callus pieces that no longer express GFP are regenerated and analyzed for expression of the foreign or agronomic gene. Agronomically useful transgenic plants are thereby produced that do not contain a marker gene.

The sensitivity of the screening method can be further increased by placing two markers genes between the FRT sequences. For example, plant cells are bombarded with a DNA construct containing the PAT and GFP genes flanked by FRT sequences and a foreign or agronomic gene. Stable transformants are recovered on bialaphos-containing medium and positive GFP-expression is confirmed. The transformed callus is then bombarded with FLP. The callus is then grown for 2–6 weeks with no selection until clear GFP-null sectors can be identified. These sectors can be transferred onto bialaphos/chlorophenol red multiwell test plates to confirm bialaphos sensitivity (i.e. within 3–5 days). Callus pieces that no longer express GFP or PAT are regenerated and analyzed for expression of the foreign or agronomic gene. This permits recovery of agronomically useful transformants without any marker genes in the final product.

Likewise, the Ac/Ds system of maize can also be used in transgenic plants to excise the screenable marker gene that is transformed together with a foreign or agronomic gene. Mobilization of Ac and/or Ds has been demonstrated in diverse plants such as tomato, tobacco and Arabidopsis. Yoder et al., In Tomato Technology, Alan R. Liss, Inc. pp 189–198 (1987); Yoder et al., U.S. Pat. No. 5,225,341; Baker et al., *EMBO J.* 6: 1547–1554 (1987) and Lawson et al. *Mol. Gen. Genet.*, 245: 608–615 (1994). Likewise, the cre/lox recombinase system from bacteriophage P1 could also be used in conjunction with GFP. Excision of transgenes in plants using the cre/lox system was first demonstrated in tobacco. Odell et al., *Mol. Gen. Genet.*, 223: 369–378 (1990) and Dale and Ow, *Proc. Natl. Acad. Sci. USA*, 88: 10558–10562 (1991). Similar to the FLP and Ac systems described above, GFP expression provides an efficient, easily scorable phenotype for monitoring excision.

3. Isolation of Nucleotide Sequences Encoding GFP

Peptide sequences from purified GFPs are used to design degenerate oligonucleotide primers for polymerase chain reactions and gene cloning. Protein extracts can be prepared from cnidarian cells by standard methods known to the art. See, for example, Harlow and Lane, Antibodies, A Laboratory Manual, Cold Spring Harbor Press, (1988). In a preferred embodiment, cnidarian cells are extracted into a buffer, and the extracts separated into membrane and soluble fractions. Each fraction is tested for green fluorescence activity in the presence of blue light.

Fractions which contain GFP activity are then purified further to determine which components are responsible for the activity. Purification of the active fractions can be carried out by methods known in the art. See, for example, PROTEIN PURIFICATION METHODS—A PRACTICAL APPROACH, Harris et al., Eds. (IRL Press, Oxford, 1989). Extracts prepared as described above are purified by sequential size exclusion chromatography isoelectric focusing, HPLC size exclusion chromatography, and chromatography on an affinity column. Fractions which display GFP activity can be analyzed further by SDS-PAGE analysis to determine the approximate molecular mass of the active component.

Purified GFPs prepared by the methods described above can be sequenced using methods well known in the art, for example using a gas phase peptide sequencer (Applied Biosystems, Foster City, Calif.). To determine as much of the peptide sequence as possible, it is preferred that the proteins of the present invention be cleaved into smaller fragments more suitable for gas-phase sequence analysis. This can be achieved by treatment of a purified GFP with selective peptidases, and in a particularly preferred embodiment, with endoproteinase lys-C (Boehringer). The fragments so produced can be separated by reversed-phase HPLC chromatography.

The peptide sequences of the proteins determined as above can be used to determine the DNA sequence encoding the protein. Methods for carrying out this determination are well known in the art. See, for example Sambrook et al., MOLECULAR CLONING: A LABORATORY MANUAL, Second Edition, (Cold Spring Harbor Laboratory Press, Cold Spring Harbor, N.Y. 1989).

In a preferred embodiment of the present invention, the peptide sequences are used to design degenerate oligonucleotide primers for polymerase chain reactions. Each degenerate primer set will preferably contain every possible DNA sequence encoding the corresponding peptide sequences. Primer sets are prepared in both the sense and antisense orientation. Suitable oligonucleotide primers can be synthesized using commercial synthesizers, such as those supplied by Applied Biosystems (Foster City, Calif.). In a particularly preferred embodiment, the primers include additional nucleotide sequences containing restriction endonuclease cleavage sites. The presence of such sites allows for the directional cloning of PCR products into suitable cloning vectors after treatment with an appropriate restriction enzyme. See Finney, "Molecular Cloning of PCR Products", in CURRENT PROTOCOLS IN MOLECULAR BIOLOGY, Ausubel et al. Eds. (John Wiley & Sons, New York, 1987) p. 15.7.1.

Template DNA for the PCR can be prepared from appropriate cnidarian cells or tissues using methods well known in the art. See Sambrook et al., supra. In a preferred embodiment, host cells are crushed under liquid nitrogen and mRNA is extracted using a commercially available kit (Pharmacia, Piscataway, N.J.).

The mRNA preparation can then be used as a template for cDNA synthesis using poly(dT) or random hexamer primers by standard techniques. See Sambrook ee al., supra. In a particularly preferred embodiment, cDNA synthesis is carried out using a commercially available kit (Pharmacia).

The cDNA can then be used directly for PCR using the method of Saiki et al., *Science* 239: 487 (1988). The cDNA also is used to prepare a cDNA library by standard methods. See Sambrook et al., supra. In a particularly preferred embodiment, the cDNA is packaged into bacteriophage particles using a commercially available kit (Promega, Madison, Wis.). The packaged cDNA is then transfected into *E. coli* to produce a cDNA library.

In an alternative preferred embodiment, genomic DNA from cnidarian cells or tissue can be used as the template DNA for the PCR. Genomic DNA can be prepared by standard methods and PCR can then be used to prepare double stranded DNA molecules to probe the cDNA library and the genomic DNA for the gene(s) encoding GFP. In a preferred embodiment, degenerate primers are prepared corresponding to the termini of the longest peptide sequence determined by peptide sequencing. In a particularly preferred embodiment, primers are used in a PCR with first strand cDNA as template to amplify the DNA encoding the peptide. PCR is carried out under standard conditions. See Sakai et al., supra.

PCR amplification products are analyzed by polyacrylamide gel electrophoresis using standard methods. If an amplification product of the expected size (based on the peptide sequence) is found, the product is digested with appropriate restriction enzymes, ligated into a cloning vector and cloned by standard methods. See Sambrook et al, supra. In a preferred embodiment, clones are sequenced to verify that sequences according to the expected peptide sequence are present.

Once the DNA sequence encoding the peptide is known, it can be used to prepare non-degenerate primers corresponding to that sequence, again containing restriction enzyme recognition sequences to aid in cloning of DNA products. These primers are used in combination with degenerate primers corresponding to other peptide sequences to generate PCR amplification products which can be cloned and then analyzed as above. By these means, fragments of the gene sequence of the protein can be determined. Alternative methods for carrying out this PCR analysis include use of the 5' or 3' RACE methods using commercially available kits, such as those manufactured by Life Technologies (Gaithersburg, Md.) or Clontech (Palo Alto, Calif.). Primers for this method are selected according to the manufacturer's directions.

Gene fragments prepared as above are excised from the cloning vector by restriction enzyme digestion, labeled with $^{32}$P by conventional methods and used as probes to identify the complete gene encoding the protein from within a cDNA or genomic library. In a preferred embodiment, the probe is chosen such that it is long enough to ensure hybridization specificity, while remaining short enough to allow reasonable rates of hybridization to the target gene.

A cnidarian genomic DNA library can be prepared by means well-known in the art. See, for example, Slightom et al. "Construction of λ Clone Banks", in METHODS IN PLANT MOLECULAR BIOLOGY AND BIOTECHNOLOGY, Glick et al. (eds.), pages 121–146 (CRC Press, 1993). Genomic DNA can be isolated from cnidarian tissue, for example, by lysing plant tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient. See, for example, Ausubel et al. (eds.), CURRENT PROTOCOLS IN MOLECULAR BIOLOGY, pages 2.3.1–2.3.3 (Wiley Interscience 1990) ["Ausubel"].

DNA fragments that are suitable for the production of a genomic library can be obtained by the random shearing of genomic DNA or by the partial digestion of genomic DNA with restriction endonucleases. See, for example, Ausubel at pages 5.3.2–5.4.4, and Slightom et al., supra. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are disclosed by Slightom et al., supra, and are well-known in the art. Also see Ausubel at pages 3.0.5–3.17.5.

Screening of the cDNA or genomic library is carried out by conventional methods. See Sambrook et al, supra. Clones which hybridize to the probe are purified and their sequences determined. To facilitate sequencing, nested deletions in the clones can be created using standard protocols, or by commercially available kits such as Erase-a-base (Promega, Madison, Wis.) or The Deletion Factory (Life Technologies, Gaithersburg, Md.), following the manufacturer's instructions. The sequences obtained are analyzed for the presence of open reading frames by conventional methods and to check if the entire gene sequence has been found. In a preferred embodiment, cDNA libraries are prepared by both random hexamer and poly (dT) priming from samples, and are used to maximize the chances of finding the complete coding sequence of the desired gene.

Once the entire coding sequence of the gene for GFP has been determined, the gene can be inserted into an appropriate expression system. The gene can be expressed in any number of different recombinant DNA expression systems to generate large amounts of protein, which can then be purified.

4. Chemical Synthesis of Genes Encoding GFP

Once the amino acid sequence of a GFP is known, a gene encoding this GFP can be synthesized. In addition, the nucleotide sequence of a synthetic gene encoding GFP can be optimized for expression in plants by modifying the codon usage to include plant preferred codons. See, for example, Murray et al., *NAR* 17: 477 (1989). Even more specifically, the nucleotide sequence of a synthetic gene encoding GFP can be optimized for expression in monocotyledonous or dicotyledonous plants. See, for example, Campbell et al., *Plant Physiol.* 92: 1 (1990).

Genes encoding GFP can be obtained, for example, by synthesizing the genes with mutually priming long oligonucleotides. See, for example, Ausubel at pages 8.2.8 to 8.2.13. Also, see Wosnick et al., *Gene* 60:115 (1987). Moreover, current techniques using the polymerase chain reaction provide the ability to synthesize genes as large as 1.8 kilobases in length. Adang et al., *Plant Molec. Biol.* 21: 1131 (1993); Bambot et al., *PCR Methods and Applications* 2: 266 (1993).

5. Identification of Functional Fragments of the GFP

DNA clones can be analyzed using a variety of techniques such as restriction analysis, Southern analysis, primer extension analysis, and DNA sequence analysis. Primer extension analysis or S1 nuclease protection analysis, for example, can be used to localize the putative start site of transcription of the cloned gene. Ausubel at pages 4.8.1–4.8.5; Walmsley et al., "Quantitative and Qualitative Analysis of Exogenous Gene Expression by the S1 Nuclease Protection Assay," in METHODS IN MOLECULAR BIOLOGY, VOL. 7: GENE TRANSFER AND EXPRESSION PROTOCOLS, Murray (ed.), pages 271–281 (Humana Press Inc. 1991). Functional fragments of the GFP protein are identified by production of green fluorescence in the presence of blue UV light.

The general approach of such functional analysis involves subcloning DNA fragments of a genomic clone, cDNA clone or synthetic gene sequence into an expression vector, introducing the expression vector into a heterologous host, and screening to detect green fluorescence in the presence of UV to blue light. Methods for generating fragments of a cDNA or genomic clone are well-known. Variants of an isolated DNA encoding GFP can be produced by deleting, adding and/or substituting nucleotides for the isolated nucleotides, for example, the nucleotide sequence of SEQ ID NO: 1. Such variants can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also see generally, McPherson (ed.), DIRECTED MUTAGENESIS: A PRACTICAL APPROACH, (IRL Press 1991). Thus, the present invention also encompasses DNA molecules comprising nucleotide sequences that have substantial sequence similarity with SEQ ID NO: 1 and encode a GFP.

6. Methods for Plant Transformation

The GFP-based screening method for plant transformation of the instant application can be used in conjunction with any method of plant transformation and regeneration. Numerous methods for plant transformation have been developed, including biological and physical, plant transformation protocols. See, for example, Miki et al., "Procedures for Introducing Foreign DNA into Plants" in *Methods in Plant Molecular Biology and Biotechnology,* Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology,* Glick, B. R. and Thompson, J. E. Eds. (CRC Press, Inc., Boca Raton, 1993) pages 89–119.

A. Agrobacterium-mediated Transformation

The most widely utilized method for introducing an expression vector into plants is based on the natural transformation system of Agrobacterium. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C.I., *Crit. Rev. Plant. Sci.* 10: 1 (1991). Descriptions of Agrobacterium vector systems and methods for Agrobacterium-mediated gene transfer are provided by Gruber et al., supra, Miki et al., supra, and Moloney et al., *Plant Cell Reports* 8: 238 (1989).

B. Direct-Gene Transfer

Despite the fact the host range for Agrobacterium-mediated transformation is broad, some major cereal crop species and gymnosperms have generally been recalcitrant to this mode of gene transfer, even though some success has recently been achieved in rice. Hiei et al., *The Plant Journal* 6: 271–282 (1994). Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988) Sanford, J. C., *Physiol. Plant* 79: 206 (1990), Klein et al., *Biotechnology* 10: 268 (1992).

Another method for physical delivery of DNA to plants is sonication of target cells. Zhang et al., *Bio/Technology* 9: 996 (1991). Alternatively, liposome or spheroplast fusion have been used to introduce expression vectors into plants.

Deshayes et al., *EMBO J.*, 4: 2731 (1985), Christou et al., *Proc Natl. Acad. Sci. U.S.A.* 84: 3962 (1987). Direct uptake of DNA into protoplasts using $CaCl_2$ precipitation, polyvinyl alcohol or poly-Lornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2–38, p 53 (1990); D'Halluin et al., *Plant Cell* 4: 1495–1505 (1992) and Spencer et al., *Plant Mol. Biol.* 24: 51–61 (1994).

A preferred method is microprojectile-mediated bombardment of immature embryos. The embryos can be bombarded on the embryo axis side to target the meristem at a very early stage of development or bombarded on the scutellar side to target cells that typically form callus and somatic embryos. Targeting of the scutellum using projectile bombardment is well known to those in the art of cereal tissue culture. Klein et al., *Bio/Technol.*, 6: 559–563 (1988); Kartha et al., *Plant Cell Rep.* 8: 429–432 (1989); Sautter et al., *Bio/Technol.*, 9: 1080–1085 (1991); Chibbar et al., *Genome*, 34: 415–460 (1991). The scutellar origin of regenerable callus from cereals is well known. Green et al., *Crop Sci.*, 15: 417–421 (1975); Lu et al., *TAG* 62: 109–112 (1982); and Thomas and Scott, *J. Plant Physiol.* 121: 159–169 (1985). Targeting the scutellum and then using chemical selection to recover transgenic plants is well established in cereals. D/Halluin et al., *Plant Cell* 4: 1495–1505 (1992); Perl et al., *MGG* 235: 279–284 (1992); Cristou et al., *Bio/Technol.* 9: 957–962 (1991). This literature reports DNA targeting of the scutellum and recovery of transgenic callus, plants and progeny based on a chemical selection regime. None of these references teach successful plant transformation wherin transformed cells are: visualized with a screenable marker such as GUS.

A preferred transformation method involves bombardment of the scutellar surface of immature embryos to introduce a fGP expression cassette and any other cotransformed genes. Embryos can be pretreated for 1 to 48 hours with a high osmoticum medium or left on a high-osmoticum medium for 24–48 hours after bombardment to improve cell survival and transformation frequencies. Immature embryos are then cultured on typical callusinducing medium with no selective agent. At each subculture transfer, i.e., every two weeks, the culture is monitored using UV-blue light for GFP fluorescence. Fluorescing calli are separated from non-fluorescing callus, and grown to the point where plants can be regenerated through standard media progressions.

Many exemplary variations, in terms of target cells and tissue culture routes are known in the art that could be used with GFP in this fashion. Some of these variations include introduction of GFP expression into protoplasts, suspension cells, type II callus, and type I callus, as in Morocz et al., *Theor. Appl. Genet.* 80: 721–726 (1990), Gordon-Kamm et al., *Plant Cell* 2: 603–618 (1990), Fromm et al., *Bio/Technol.* 8: 833–839 (1990) and D'Halluin et al., *Plant Cell* 4: 1495–1505 (1992). Microspores and microspore-derived embryogenic callus also represent a feasible alternative target/culturing route for using GFP screening to recover transformants. See Sun et al., *Plant Cell Rep.* 8: 313–316 (1989) and Mitchell et al., *J. Plant Physiol.* 37: 530–536 (1991). Furthermore, it is expected that the method of the present invention is also be applicable to any dicot species that is known to have a callus stage, for example, tobacco, canola or soybean.

In the case of the maize meristem target, the method entails selective enlargement of transgenic sectors, toward genetic homogeneity, in cell layers that contribute to germline transmission. This method is described in copending U.S. patent application Ser. No. 08/483,091, now U.S. Pat. No. 5,736,369, incorporated herein by reference, and comprises the steps of (A) introducing foreign DNA into a meristem that is not enclosed by sheathing leaves; (B) inducing reorganization of the meristem to increase transgenic sector size, whereby the likelihood that a transgenic sector will contribute to germline transmission is increased; and (C) exposing the meristem to conditions under which it differentiates to form a plantlet, wherein the plantlet contains the transgenic sector or is homogeneously transformed by the foreign DNA, such that the plantlet can be grown into a transformed cereal plant that will transmit the foreign DNA to progeny. The foreign DNA can be introduced into a plurality of meristems, at least some of which differentiate in step (C) to form a plurality of plantlets.

In one preferred embodiment, reorganization is effected through at least one manipulation selected from the group consisting of (i) imposition of a nonlethal selective pressure on the meristems, (ii) mechanically-induced meristem reorganization, and (iii) hormonally-induced shoot multiplication. In another preferred embodiment the conditions in step (C) are such that the meristems undergo maturation and plant differentiation to form shoot apices, and the method further comprises effecting reorganization of meristem tissue in the shoot apices to enlarge transformed sectors or to produce periclinal L2 chimeras. The reorganization in this regard can be effected, for example, by exposing the shoot apices to nonlethal selection pressure such that transformed cells have a competitive growth advantage over nontransformed cells in the shoot apices, and the proportion of transformed cells in the shoot apices is increased. In yet another preferred embodiment, the method further comprises a step before step (B), e.g., before step (A), of wounding the apical dome selectively. A method of the present invention also can comprise the further steps of (i) dissecting out an axillary bud from above the base of a leaf of a plantlet when a chimeric sector is observed in a substantial portion of the leaf, and then (ii) germinating the axillary bud into a whole plant or subjecting the axillary bud to shoot multiplication.

Likewise, the introduction of GFP-encoding DNA into dicot meristems provides an efficient method of mapping transgenic sectors and following these up into a germline and into progeny. Using mature imbibed seeds as the starting material, the meristem is exposed by removal of the cotyledons, and DNA is introduced into meristem cells. A preferred method for introducing DNA into meristem cells is Agrobacterium-mediated delivery, but other DNA delivery methods can be used with this explant such as bombardment with DNA-coated particles, or silicon carbide fiber-mediated delivery. Kaeppler et al., *Plant Cell Rep.* 9: 415–418 (1990) After DNA introduction, the meristem explants are cultured.

Plants can be manipulated, for example, by removal of the apical meristem, to stimulate axillary or secondary buds which can exhibit larger transgenic sectors relative to the primary shoot. Flowers above transgenic shoots are pollinated and the progeny are analyzed for transgene presence and expression. A variety of starting explants can regenerate shoots in sunflower, and thus represent alternative targets for GFP-encoding DNA delivery and transmission to progeny. These include the seedling meristem (as above), also the seedling hypocotyl, the mature cotyledon, the immature cotyledon, zygotic immature embryos, somatic embryos, and primary leaflets. See for example, respectively, Greco et al., *Plant Sci. Lett.* 36: 73–77 (1984); Krauter et al., Helia 14: 117–122 (1991); Power Am. J. Bot. 74: 497–503 (1987); Krauter et al., Theor. Appl. Genet. 82: 521–525 (1991); Finer, Plant Cell Rep. 6: 372–374 (1987), and Greco et al., Plant Sci. Lett. 36: 73–77 (1984).

In similar fashion, GFP expression could be used in other dicot species, for example, soybean, to map sectors and/or identify transformants and follow the transgenes through to progeny. A GFP-encoding cassette and other cotransformed genes can be introduced into soybean cotyledonary node cells using Agrobacterium. The explants are cultured on Gamborg (B5) medium with or without kanamycin selection. With no selection, GFP expression is used to identify transgenic chimeric or homogeneously transformed plantlets, which are rooted, grown to maturity and pollinated in the greenhouse. Progeny seed are collected for analysis. The use of cotyledonary nodes and Agrobacterium is presented by way of example, but other target cells and culturing methods could be used with GFP for soybean. In addition to the cotyledonary node cells, mature cotyledons and immature cotyledons have both been used for transformation. See Hinchee et al., Bio/Technol. 915–922 (1988) and Parrott et al., Plant Cell Rep. 7: 615–617 (1989). Meristems from immature soybean seed embryonic axes have also been used for bombardment-mediated soybean transformation. See Christou et al., Plant Physiol. 87: 671–674 (1988) and McCabe et al., Bio/Technol. 6: 923–926 (1988).

7. Promoters

A. Inducible Promoters

An inducible promoter is operably linked to a nucleotide sequence encoding a GFP. Optionally, the inducible promoter is operably linked to a nucleotide sequence encoding a signal sequence which is operably linked to a nucleotide sequence encoding GFP. With an inducible promoter the rate of transcription increases in response to an inducing agent.

Any inducible promoter can be used in the instant invention. See Ward et al. Plant Mol. Biol. 22: 361–366 (1993). Exemplary inducible promoters include that from the ACE1 system which responds to copper (Mett et al. PNAS 90: 4567–4571 (1993)); In2 gene from maize which responds to benzenesulfonamide herbicide safeners (Hershey et al., Mol. Gen. Genetics 227: 229–237 (1991) and Gatz et al., Mol. Gen. Genetics 243: 32–38 (1994)) or Tet repressor from Tn10 (Gatz et al., Mol. Gen. Genet. 227: 229–237 (1991). A particularly preferred inducible promoter is a promoter that responds to an inducing agent to which plants do not normally respond. An exemplary inducible promoter is the inducible promoter from a steroid hormone gene the transcriptional activity of which is induced by a glucocorticosteroid hormone. Schena et al., Proc. Natl. Acad. Sci. U.S.A. 88: 10421 (1991).

The expression vector comprises an inducible promoter operably linked to a nucleotide sequence encoding GFP. The expression vector is introduced into plant cells and presumptively transformed cells are exposed to an inducer of the inducible promoter. The cells are screened for the presence of GFP protein by means of illuminating the cells with UV to blue light and screening for the presence of green fluorescence.

B. Tissue-specific or Tissue Preferred Promoters

A tissue-specific promoter is operably linked to a nucleotide sequence encoding a GFP. Optionally, the tissue-specific promoter is operably linked to a nucleotide sequence encoding a signal sequence which is operably linked to a nucleotide sequence encoding GFP. Plants transformed with a gene encoding GFP operably linked to a tissue-specific promoter produce the GFP protein exclusively, or preferentially, in a specific tissue.

Any tissue-specific or tissue-preferred promoter can be utilized in the instant invention. Exemplary tissue-specific or tissue-preferred promoters include a root-preferred promoter such as that from the phaseolin gene (Murai et al., Science 23: 476–482 (1983) and Sengupta-Gopalan et al., Proc. Natl. Acad. Sci. USA 82: 3320–3324 (1985)); a leaf-specific and light-induced promoter such as that from cab or rubisco (Simpson et al., EMBO J. 4(11): 2723–2729 (1985) and Timko et al., Nature 318: 579–582 (1985)); an anther-specific promoter such as that from LATS2 (Twell et al., Mol. Gen. Genet. 217: 240–245 (1989)); a pollen-specific promoter such as that from Zm13 (Guerrero et al., Mol. Gen. Genet. 224: 161–168 (1993)) or a microspore-preferred promoter such as that from apg (Twell et al., Sex. Plant Reprod. 6: 217–224 (1993).

The expression vector comprises a tissue-specific or tissue-preferred promoter operably linked to a nucleotide sequence encoding GFP. The expression vector is introduced into plant cells. The cells are screened for the presence of GFP protein by means of illuminating the cells with UV to blue light and screening for the presence of green fluorescence.

C. Constitutive Promoters

A constitutive promoter is operably linked to a nucleotide sequence encoding a GFP or the constitutive promoter is operably linked to a nucleotide sequence encoding a signal sequence which is operably linked to a nucleotide sequence encoding GFP.

Many different constitutive promoters can be utilized in the instant invention. Exemplary constitutive promoters include the promoters from plant viruses such as the 35S promoter rom CaMV (Odell et al., Nature 313: 810–812 (1985) and the promoters from such genes as rice actin (McElroy et al., Plant Cell 2: 163–171 (1990)); ubiquitin (Christensen et al., Plant Mol. Biol. 12: 619–632 (1989) and Christensen et al., Plant Mol. Biol. 18: 675–689 (1992)); pEMU (Last et al., Theor. Appl. Genet. 81: 581–588 (1991)); MAS (Velten et al., EMBO J. 3: 2723–2730 (1984)) and maize H3 histone (Lepetit et al., Mol. Gen. Genet. 231: 276–285 (1992) and Atanassova et al., Plant Journal 2(3): 291–300 (1992)).

The ALS promoter, a XbaI/NcoI fragment 5-prime to the Brassica napus ALS3 structural gene (or a nucleotide sequence that has substantial sequence similarity to said XbaI/NcoI fragment), represents a particularly useful constitutive promoter. Co-pending Pioneer Hi-Bred International U.S. patent application Ser. No. 08/409,297, now U.S. Pat. No. 5,659,026.

The expression vector comprises a constitutive promoter operably linked to a nucleotide sequence encoding GFP. The expression vector is introduced into plant cells and presumptively transformed cells are screened for the presence of GFP protein by means of illuminating the cells with UV to blue light and screening for the presence of green fluorescence.

8. Signal Sequences for Targeting Proteins to Subcellular Compartments

Transport of GFP to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5-prime and/or 3-prime region of a gene encoding GFP. Targeting sequences at the 5-prime and/or 3-prime end of the structural gene may determine, during protein synthesis and processing, where the encoded protein is ultimately compartmentalized. The presence of a signal sequence directs a polypeptide to either an intracellular organelle or subcellular compartment or for secretion to the apoplast.

In addition to the targeting sequences described above, the addition of amino acids to the encoded protein (fusing GFP to either another protein, a protein fragment, or a peptide) can further influence the fate of GFP. For example, a nuclear localization signal (NLS) alone is not sufficient to accumulate GFP in the nucleus. The GFP protein is sufficiently small that it freely diffuses from the nucleus into the cytoplasm, probably through the nuclear pores. The fusion of GFP to a sufficiently large protein permits accumulation in the nucleus if the GFP protein also contains an NLS at the amino-terminus. GFP can also be targeted to the nucleus by fusing GFP to proteins that are normally targeted to the nucleus.

The following exemplary signal sequences were utilized for targeting of GFP. However, the invention encompasses use of any signal sequence, or combination of signal sequences, to facilitate transport of GFP to a subcellular compartment or the apoplast where the protein is not toxic to the cell but can be detected.

More specifically, GFP is expressed in plant cells transformed with a expression vector carrying a nucleotide sequence encoding a signal sequence(s), which directs a protein to a subcellular compartment or to the apoplast, operably linked to a gene encoding GFP. This GFP gene construct can be expressed from a constitutive, tissue-specific, tissue-preferred or inducible promoter. GFP is transported to a subcellular compartment or the apoplast where it is not toxic to the-plant cell. Cells illuminated with UV to blue light can be detected because they emit green fluorescence. The transformed cells are selected for regeneration. If the expression vector also carries a gene encoding a foreign protein or agronomically useful protein, the regenerated plant can be used for production of this protein.

protein that extends beyond the procesing site (marked by*) (SEQ ID NOS 3 & 4).

```
ATG GCG TCC TCC ACG ATG GCC CTC TCC TCC ACC GCC
M   A   S   S   T   M   A   L   S   S   T   A

TTC GCC GGC AAG GCC GTG AAC GTG CCG TCG TCG TCC
F   A   G   K   A   V   N   V   P   S   S   S

GCC TTC GAG GCC CGC GTG ACC ATG AGG AAG ACG GCG
A   F   E   A   R   V   T   *M  R   K   T   A

GCG AAG GCC AAG CCA GCT GCG GCG TCC GGG AGC CCG
A   K   A   K   P   A   A   A   S   G   S   P

TGG TAC GGC CCC ATG
W   Y   G   P   M
```

B. PHP8087—CPN60::GFPm

The mitochondrial signal sequence from the maize chaperonin 60 gene is shown below. Close, P. S., Master's Theses, Iowa State University (1993). The signal sequence includes intron 1 of cpn60II (marked by –) and includes two amino acids from the cpn60II protein beyond the processing site (marked by *) (SEQ ID NOS 5 & 6).

```
ATG TAC CGC GCG GCC GCT AGC CTC GCC TCC AAG GCG CGG CAA GCC GGG AGC
M   Y   R   A   A   A   S   L   A   S   K   A   R   Q   A   G   S

AGC TCC GCC GCT CGC CAG-gtgagagcagactcgtgtttatacgcgtgtgatgggtctgatg
S   S   A   A   R   Q gaggatcccgccctcagatttggtaatgttggcctggggttctagtagttctgcgtgcagggctgtg ggtttgctgcatggtgctgtttattttggtggcgatctgccggaatctgtagttcgctcgcgcaaaa tctaagctagctcgctaatggcgtactggcgtggggtttcacattaatctacggtggtgaactcgtc actaccgtcctccagttagctgttagacaccgaatacactgattggcagttgagaaacattgatctg atccagcagaaatcgatgtcttgtgaaattcgttatttattgtcgtgtaaccttggggcatggcag tctctaattgatcacgcactcacctctgttgtgtgatgcttttatag-GTT GGA AGC AGG CTT
                                                  V   G   S   R   L

GCC TGG AGC AGG AAC TAT GCT GCC ATG
A   W   S   R   N   Y   *A  A   M
```

C. PHP8144—Ubi::BAA-GFPm—Cloned sequence includes 1 amino acid beyond processing site (marked by *, lower case bases show linker sequence).

The barley alpha amylase 1 signal sequence is shown below. Knox, C., et al., "Strucutre and Organization of Two Divergent Alpha-Amylase Genes From Barley", Plant Mol. Biol. 9:3–17 (1987). The cloned sequence includes sequence only up to processing site. (SEQ ID NOS 7 & 8).

```
ATG GCC AAC AAG CAC CTG AGC CTC TCC CTC TTC CTC GTG CTC CTC GGC CTC TCC
M   A   N   K   H   L   S   L   S   L   F   L   V   L   L   G   L   S

GCC TCC CTC GCC TCC GGA tcc ATG
A   S   L   A   S   *G  S   M
```

A. PHP8080—Ubi::CTP-GFPm

A chloroplast signal sequence from the maize cab-m7 ahs been characterized and the nucleotide sequence is shown below. Becker et al., Plant Mol. Biol. 20: 49 (1992). The signal sequence includes 21 amino acids of the cab-m7

D. PHP8757—Ubi::BAA-GFPm-BLVT—Signal sequence starts at *, lower case bases show linker sequence.

The barley lectin vacuole signal sequence is shown below. Lerner et al., Plant Physiol. 91: 124–129 (1989). (SEQ ID NOS 9 & 10).

```
AAG atc tac GTG TTC GCC GAG GCC ATC GCC GCC AAC TCC ACC CTC GTG GCC GAG
K   I   Y  *V  F   A   E   A   I   A   A   N   S   T   L   V   A   E
```

E. PHP8758—Ubi::BAA-GFPm-HDEL—Signal sequence starts at *, lower case bases show linker sequence.

The HDEL endoplasmic reticulum retention signal from maize b-70 is shown below. Fontes et al., Plant Cell 3: 483–496 (1991). (SEQ ID NOS 11 & 12).

```
AAG atc tac GAC GGC GGC GTG GAC GAC GAC CAC GAC
K   I   Y  *D  G   G   V   D   D   D   H   D

GAG CTC
E   L
```

F. PHP8759—Ubi::BAA-SVT-GFPm—Marked by lower case bases show linker sequence.

The sweet potato sporamin vacuole signal sequence is shown below. Matsuoka et al., Proc. Natl. Acad. Sci. 88: 834 (1991). The sequence shown includes 4 additional sporamin amino acids beyond the processing site (marked by *). (SEQ ID NOS 13 & 14).

```
ATG GCC AAC AAG CAC CTG AGC CTC TCC CTC TTC CTC
M   A   N   K   H   L   S   L   S   L   F   L

GTG CTC CTC GGC CTC TCC GCC TCC CTC GCC TCC GAA
V   L   L   G   L   S   A   S   L   A   S   G

CAC AGC AGG TTC AAC CCC ATC AGG CTG CCC ACC ACC
H   S   R   F   N   P   I   R   L   P   T   T

CAC GAG CCC GCC AGC AGC GAG ACC gga tcc ATG
H   E   P   A  *S   S   E   T   G   S   M
```

G. PHP8882—Ubi::GFPm-SKL—(marked by *)

The consensus peroxisome signal sequence designated SLK is shown below. Gould et al., J. Cell Biol 108: 1657 (1989). (SEQ ID NOS 15 & 16).

```
           AAG TCG AAG CTT
           K  *S   K   L
```

H. Ubi::GR-GFPm

The pea glutathione reductase mitochondrial and chloroplast signal sequence is shown below. Creissen et al., Plant J. 2: 129 (1991). The sequence shown includes 20 additional amino acids beyond the putative processing site (marked by *) (SEQ ID NOS 17 & 18).

```
ATG AAC CAG GCG ATG GCC ACC CCG CTG TCC CTG TCC
M   N   Q   A   M   A   T   P   L   S   L   S

TGC TGC TCC CCG ACC CTG ACC AGG TCC ACC CTG TTC
C   C   S   P   T   L   T   R   S   T   L   F

TTC ACC AAG ACC TTC CCG TTC TCC CGC TCC TTC TCC
F   T   K   T   F   P   F   S   R   S   F   S

ACC CCG CTG CCG CTG TCC ACC AAG ACC CTG ATC TCC
T   P   L   P   L   S   T   K   T   L   I   S

CTG TCC CCG CCG CAC AGG ACC TTC GCC GTG AGG GCT
L   S   P   P   H   R   E   S   Q   N   G   A

GAG TCC CAG AAC GGC GCG GAC CCG GCC AGG CAG TAC
D   P   A   R   Q   Y   D   F   D   L   F   T
```

-continued
```
GAC TTC GAC CTG TTC ACC ATC GGC
I   G   T   F   A   V  *R   A
```

I. PHP9053—Ubi::NLS-GFPm-MALS

The nuclear localization signal from simian virus 40 (SV40) was fused to the N terminus of GFPm. In order to retain the protein in the nucleus the molecular weight of NLS-GFPm was increased by making a carboxy terminal addition of the large unrelated protein maize acetolactate synthase (ALS) (lower case bases show linker sequence). Kladeron, D., Robers, B., Richardson, W., and Smith A., "A short amino acid sequence able to specify nuclear location", Cell 39: 499–509 (1984). (SEQ ID NOS 19 & 20).

```
CCG CCC AAG AAG AAG CGC AAG GTG ccc ATG ...
P   P   K   K   K   R   K   V   P   M AAG atc cac ATG
K   I   H   M
```

J. Ubi::GFPm-HRGP

A carboxy terminal fusion of a portion of the maize HRGP coding sequence to GFPm was used to anchor GFP to the cell wall. Sequence encoding amino acids 177 to 328 was used. Stiefel, V., Ruiz-Avila, L., Raz R., Valles M., Gomez J., Pages M., Martinez-Izquierdo J., Ludevid M., :Landale J., Nelson T., and Puigdomenech P., "Expression of a maize cell wall hydroxyproline-rich glycoprotein gene in early leaf and root vascular differentiation", Plant Cell 2: 785–793 (1990). (SEQ ID NOS 21 & 22).

```
TAC ACT CCA AGC CCT AAG CCA CCG GCT ACC AAG CCT
Y   T   P   S   P   K   P   P   A   T   K   P

CCC ACG CCC AAG CCG AAC CCG CCA ACG TAC ACC CCT
P   T   P   K   P   T   P   P   T   Y   T   P

TCG CCA AAG CCT CCG ACA CCC AAG CCG ACC CCG CCG
S   P   K   P   P   T   P   K   P   T   P   P

ACG TAC ACC CCT TCT CCC AAG CCT CCG ACG CCC AAG
T   Y   T   P   S   P   K   P   P   T   P   K

CCG ACC CCG CCG ACG TAC ACT CCA AGC CCC AAG CCT
P   T   P   P   T   U   T   P   S   P   K   P

CCC ACA CAC CCG ACG CCC AAG CCG ACC CCA CCG ACG
P   T   H   P   T   P   K   P   T   P   P   T

TAC ACC CCT TCC CCA AAG CCT CCG ACG CCC AAG CCG
Y   T   P   S   P   K   P   P   T   P   K   P

ACC CCA CCG ACG TAC ACC CCT TCC CCA AAG CCT CCG
T   P   P   T   Y   T   P   S   P   K   P   P

ACA CCC AAG CCG ACC CCA CCG ACG TAC ACC CCT TCC
T   P   K   P   T   P   P   T   Y   T   P   S

CCA AAG CCT CCG ACA CCC AAG CCG ACC CCA CCG ACG
P   K   P   P   T   P   K   P   T   P   P   T

TAC ACT CCC ACA CCG AAG CCG CCG GCC ACC AAG CCG
Y   T   P   T   P   K   P   P   A   T   K   P

CCC ACC TAC ACT CCG ACG CCG CCG GTG TCT CAC ACC
P   T   Y   T   P   T   P   P   V   S   H   T
```

```
                        -continued

CCC AGC CCG CCG CCA CCA TAC TAC
 P   S   P   P   P   P   Y   Y
```

K. Ubi::GFPm-SOD

Superoxide dismutase coding sequence fused to GFPm. Alcendor D., Chapman G., and Beaman B., "Isolation, sequencing and expressoin of the superoxide dismutase-encoding gene (sod) of *Nocardia asteroides* strain GUH-2", Gene 164: 143–147 (1995). (SEQ ID NOS 23 & 24).

```
GTG GCT GAG TAC ACG CTG CCG GAT CTG GAT TAC GAC
 V   A   E   Y   T   L   P   D   L   D   Y   D

TAC AGC GCC TGG AAC CCC ACA TCT CCG GGC AGA TCA
 Y   S   A   L   E   P   H   I   S   G   Q   I

ACG AGC TGA CAC CAT TCC AAG CAC CAC GCC GCC TAC
 N   E   L   H   H   S   K   H   H   A   A   Y

GTC GCC GGT GCC AAC ACG GCA CTG GAG AAG CTG GAA
 V   A   G   A   N   T   A   L   E   K   L   E

GCC GCC CGT GAG GCC GGC GAT CAC AGC GCG ATC TTC
 A   A   R   E   A   G   D   H   S   A   I   F

CTG CAC GAG AAG AAC CTC GCG TTC CAC CTC GGC GGA
 L   H   E   K   N   L   A   F   H   L   G   G

CAC GTC AAC CAC TCC ATC TGG TGG AAG AAC CTG TCC
 H   V   N   H   S   I   W   W   K   N   L   S

CCC AAC GGT GGC GAC AAG CCG GTC GGC GAG CTG GCC
 P   N   G   G   D   K   P   V   G   E   L   A

GCG GCC ATC GAC GAC CAG TTC GGT TCG TTC GAC AAG
 A   A   I   D   D   Q   F   G   S   F   D   K

TTC CGC GCG CAG TTC ACC GCC GCG GCC AAC GGC CTG
 F   R   A   Q   F   T   A   A   A   N   G   L

CAG GGC TCG GGC TGG GCG GTG CTC GGT TAC GAC ACC
 Q   G   S   G   W   A   V   L   G   Y   D   T

CTC GGC CAG AAG CTG CTG ACC TTC CAG CTC TAC GAC
 L   G   Q   K   L   L   T   F   Q   L   Y   D

CAG CAG GCC AAC GTG CCG CTG GGC ATC ATC CCG CTG
 Q   Q   A   N   V   P   L   G   I   I   P   L

CTC CAG GTC GAC ATG TGG GAG CAC GCC TTC TAC CTG
 L   Q   V   D   M   W   E   H   A   F   Y   L

CAG TAC AAG AAC GTC AAG GCC GAC TAC GTG ACC GCG
 Q   Y   K   N   V   K   A   D   Y   V   T   A

TTC TGG AAC GTC GTC AAC TGG GCC GAC GTG CAG GAC
 F   W   N   V   V   N   W   A   D   V   Q   D

CGC TTC GGC AAG GCC GTC AAC CAG GGC AAG GGC CTT
 R   F   G   K   A   V   N   Q   G   K   G   L

ATC TTC GGG
 I   F   G
```

9. Detection of GFP in Transformed Plant Cells

GFP is detected in transformed plant cells by conventional spectrophometric methods. The transformed cells or tissue are screened for the presence of GFP protein by means of the illuminating the cells with UV to blue light and screening for the presence of green fluorescence.

Compound and dissecting microscopes were fitted with appropriate filter combinations for fluorescent protein excitation. Illumination with UV-blue light (exciting around the absorption maximum of 395 nm or around the minor peak at approximately 475 nm for GFP; around 480–490 nm for the red-shifted version and around 380 nm for the blue fluorescent protein) is required for visualization. A hand-held lamp for benchtop work also permits good visualization. Cut-off filters or bandpass filters between the fluorescing tissue and the viewer (i.e. around the intermediate objective or the eyepieces of the microscope, or hand-held in front of the eyes if working on the benchtop) greatly reduced background autofluorescence from the tissue. For GFP and the red-shifted GFP this cut-off or bandpass filter permitted light between 500–550 nm to reach the viewer. For the blue fluorescent protein, this filter permitted the passage of 420 to 450 nm light. Useful filters and wavelengths are not restricted to those described above, and further generic description of the optical characteristics of this system are available. Heim et al., *Currently Biology* 6: 178–182 (1996).

Foreign Protein Genes and Agronomic Genes

With transgenic plants according to the present invention, a foreign protein can be produced in commercial quantities. Thus, the selection and propagation techniques described above yield a plurality of transgenic plants which are harvested in a conventional manner, and a foreign protein then is extracted from a tissue of interest or from total biomass. Protein extraction from plant biomass can be accomplished by known methods which are discussed, for example, by Heney and Orr, *Anal. Biochem.* 114: 92–6 (1981).

According to a preferred embodiment, the transgenic plant provided for commercial production of foreign protein is maize. In another preferred embodiment, the biomass of interest is seed. For the relatively small number of transgenic plants that show higher levels of expression, a genetic map can be generated, primarily via conventional RFLP and PCR analysis, which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR and sequencing, all of which are conventional techniques.

Likewise, by means of the present invention, agronomic genes can be expressed in transformed plants. More particularly, plants can be genetically engineered to express various phenotypes of agronomic interest. The implicated in this regard include, but are not limited to, those categorized below.

1. Genes that Confer Resistance to Pests or Disease and that Encode (A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266: 789 (1994) (cloning of the tomato Cf-9 gene for resistance to *Cladosporium fulvum*); Martin et al., *Science* 262: 1432 (1993) (tomato Pto gene for resistance to *Pseudomonas syringae* pv. tomato encodes a protein kinase);, Mindrinos et al, *Cell* 78: 1089 (1994) (Arabidopsis RSP2 gene for resistance to *Pseudomonas syringae*).

(B) A Bacillus thuringiensis protein, a derivative thereof or a synthetic polypeptide modeled thereon. See, for example, Geiser et al., *Gene* 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), under ATCC accession Nos. 40098, 67136, 31995 and 31998.

(C) A lectin. See, for example, the disclosure by Van Damme et al., *Plant Molec. Biol.* 24: 825 (1994), who disclose the nucleotide sequences of several *Clivia miniata* mannose-binding lectin genes.

(D) A vitamin-binding protein such as avidin. See, U.S. patent application Ser. No. 07/911,864, now abandoned, the contents of which are hereby incorporated by reference. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of Streptomyces nitrosporeus α-amylase inhibitor).

(F) An insect-specific hormone or pheromone such as an ecdysteroid and juvenile hormone, a variant thereof, a mimetic based thereon, or an antagonist or agonist thereof. See, for example, the disclosure by Hammock et al. *Nature* 344: 458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(H) An insect-specific venom produced in nature by a snake, a wasp, etc. For example, see Pang et al., *Gene* 116: 165 (1992), for disclosure of heterologous expression in plants of a gene coding for a scorpion insectotoxic peptide.

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(K) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(L) A hydrophobic moment peptide See U.S. patent applications Ser. No. 08/168,809 now U.S. Pat. No. 5,580,852, (disclosure of peptide derivatives of Tachyplesin which inhibit fungal plant pathogens) and Ser. No. 08/179,632 now U.S. Pat. No. 5,607,914, (teaches synhtetic antimicrobial peptides that confer disease resistance), the respective contents of which are hereby incorporated by reference.

(M) A membrane permease, a channel former or a channel blocker. For example, see the disclosure by Jaynes et al., *Plant Sci.* 89: 43 (1993), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (1994) (enzymatic inactivation in transgenic tobacco via production of single-chain antibody fragments).

(P) A virus-specific antibody. See, for example, Tavladoraki et al., *Nature* 366: 469 (1993), who show that transgenic plants expressing recombinant antibody genes are protected from virus attack.

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(R) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

2. Genes that Confer Resistance to a Herbicide, for Example
  (A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively.
  (B) Glyphosate (resistance imparted by mutant EPSP synthase and aroA genes, respectively) and other phosphono compounds such as glufosinate (PAT and bar genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).
  (C) A herbicide that inhibits photosynthesis, such as a triazine (psbA and gs+genes) and a benzonitrile (nitrilase gene). Przibilla et al., *Plant Cell* 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC accession Nos. 53435, 67441 and 67442. Cloning and expression of DNA coding for a glutathione S-transferase is described by Hayes et al., *Biochem. J.* 285: 173 (1992).

3. Genes that Confer or Contribute to a Value-Added Trait, Such as
  (A) Modified fatty acid metabolism, for example, by transforming a plant with an antisense gene of stearoyl-ACP desaturase to increase stearic acid content of the plant. See Knultzon et al., *Proc. Nat'l Acad Sci. USA* 89: 2624 (1992).
  (B) Decreased Phytate Content
    (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an Aspergillus niger phytase gene.
    (2) A gene could be introduced that reduces phytate content. In maize, this, for example, could be accomplished, by cloning and then re-introducing DNA associated with the single allele which is responsible for maize mutants characterized by low levels of phytic acid. See Raboy et al., *Maydica* 35: 383 (1990).
  (C) Modified carbohydrate composition effected, for example, by transforming plants with a gene coding for an enzyme that alters the branching pattern of starch. See Shiroza et al., *J. Bacteriol.* 170: 810 (1986) (nucleotide sequence of Streptococcus mutans fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* α-amylase), Elliot et al., *Plant Molec. Biol.* 21: 515 (1993) (nucleotide sequences of tomato invertase genes), Sogaard et al., *J. Biol. Chem.* 268: 22480 (1993) (site-directed mutagenesis of barley amylase gene), and Fisher et al., *Plant Physiol.* 102: 1045 (1993) (maize endosperm starch branching enzyme II).

EXAMPLE 1

Construction of Genes and Vectors

The GFPm nucleotide sequence was derived from a back translation of the protein sequence using maize preferred codons. Sequence analysis was performed using the Wisconsin Sequence Analysis Package from Genetics Computer Group, Madison, Wis. The nucleotide sequence was assembled from a series of synthetic oligonucleotides. Cloning sites include a 5-prime flanking BamHI restriction site, an AflIII site at the start codon, a 3-prime flanking HpaI site or a BglII site converting the stop codon to an isoleucine (FIG. 1).

Figure 4:
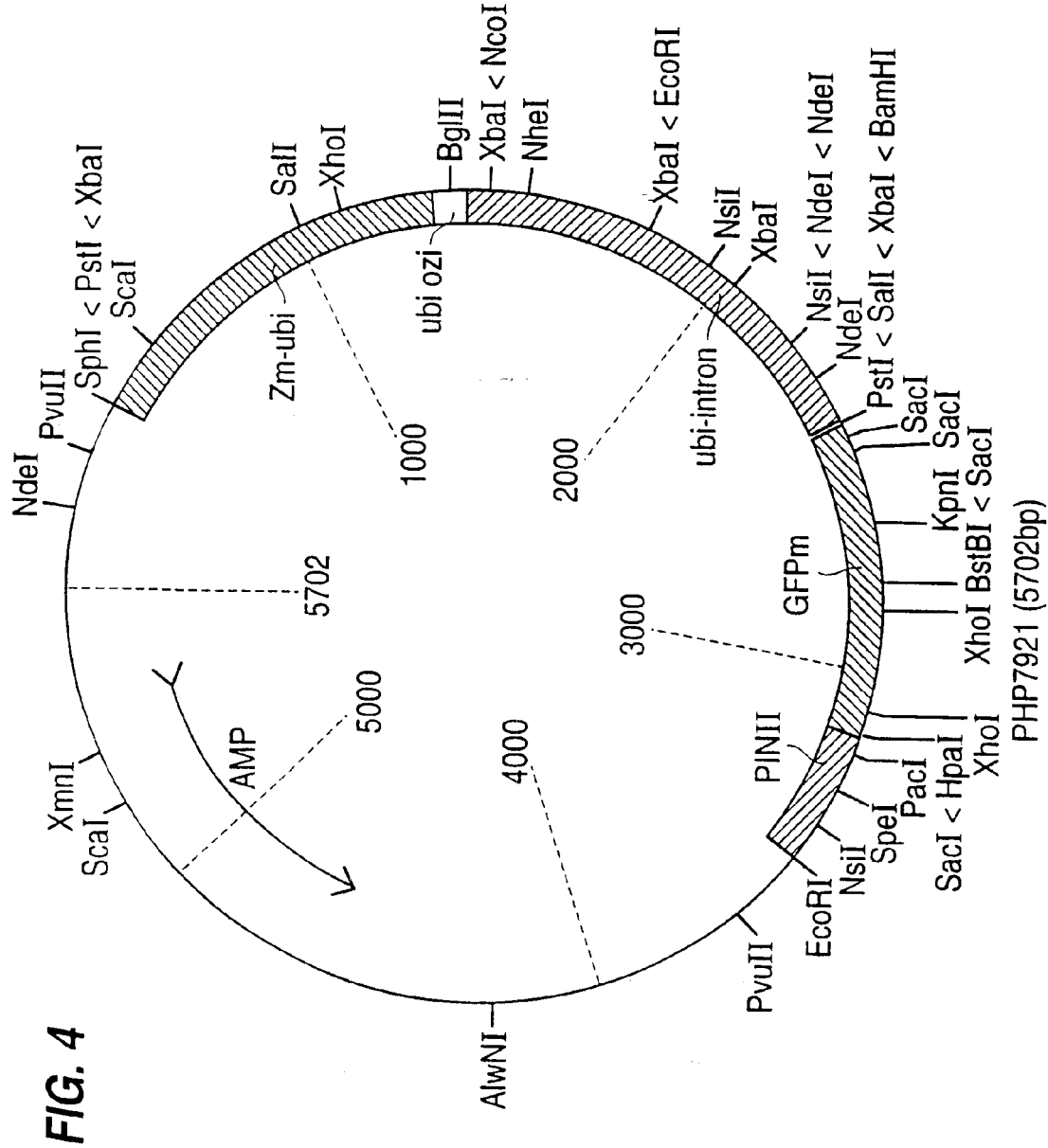
FIG. 4 shows the Plasmid Map of PHP7921.
Figure 5:
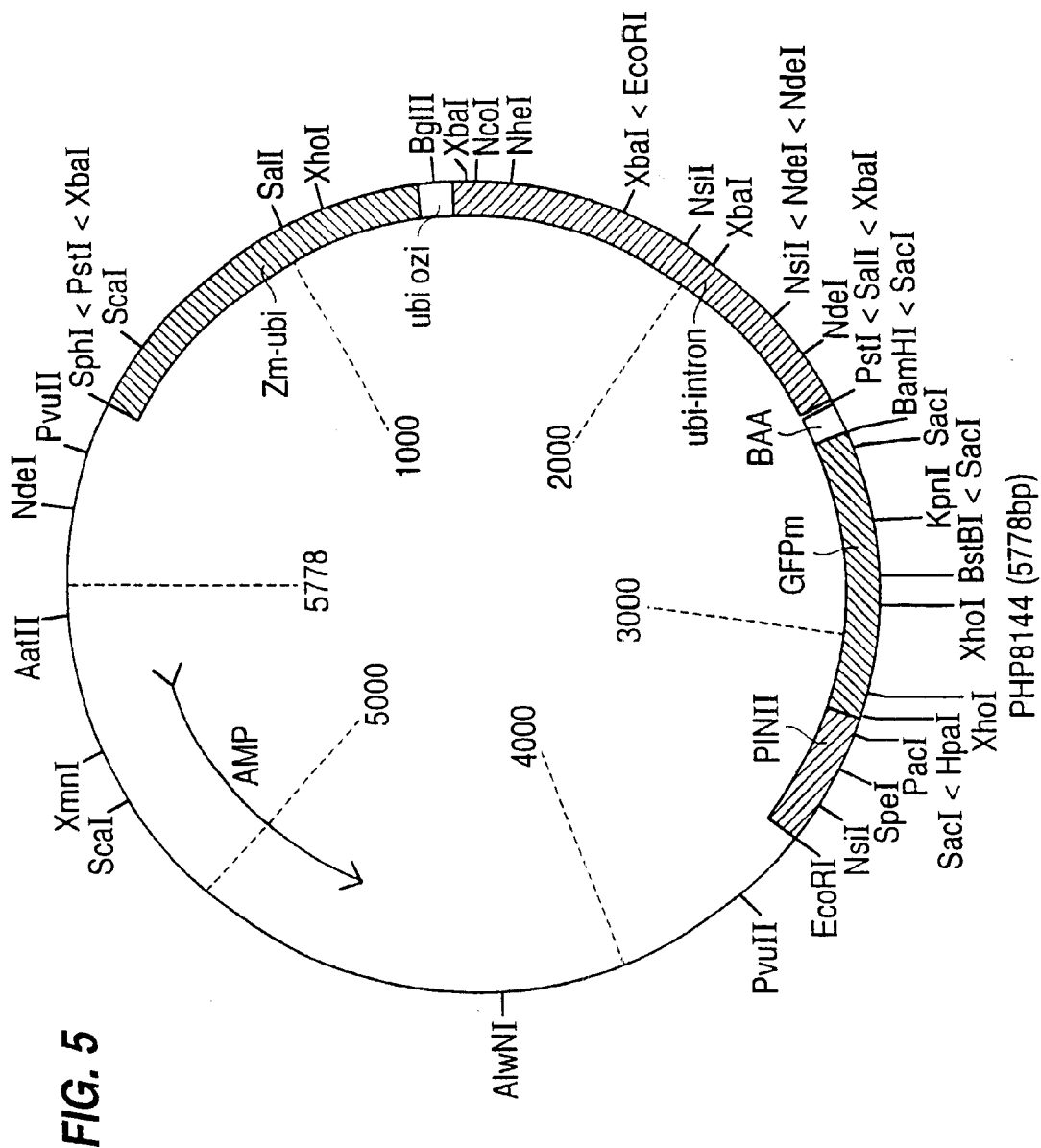
FIG. 5 shows the Plasmid Map of PHP8144.

Amino terminal fusions to GFPm were created using synthetic oligonucleotides encoding the signal sequence flanked by a 5-prime BamHI or BglII restriction site and 3-prime NcoI site. The synthetic signal sequences were cloned into PHP7921 (FIG. 4) using the 5-prime flanking BamHI and AflIII restriction sites of GFPm to create inframe fusions. Sequences cloned in this manner include the maize chloroplast signal sequence, barley alphaamylase signal sequence, pea glutathione reductase signal sequence, and SV40 nuclear localization signal. The sporamin vacuole signal sequence was synthesized with a 5-prime BspEI and 3-prime BamHI for insertion between the BAA presequence and GFPm coding sequence of pHP8144 (FIG. 5). The CPN60 promoter site, created by site-directed mutagenesis, was used with the GFPm AflIII site to make the fusion sequence. Each of plasmids PHP7921 and PHP8144 are based on pUC18.

Carboxy terminal sequences were synthesized with a 5-prime BglII and 3-prime HpaI site, and cloned into pHP7921 or pHP8144 using the 3-prime BflII and HpaI sites of GFPm. The barley lectin vacuole target, HDEL ER retention signal, SKL peroxisome signal, ALS coding sequence and HRGP coding sequence fusions were made using this strategy.

TABLE 1

PLASMIDS

| PHP Number | Target Crop | Promoter | Targeting 5' Sequence | Targeting 3' Sequence | Localized To: | Other 5' Sequences | Structural Gene | 3' Sequence | Comments |
|---|---|---|---|---|---|---|---|---|---|
| 7956 | maize | 4xERE | — | — | Cytoplasm | Omega Prime (O') Adh1 intron I | GFPm | pinII | Estrogen-inducible expression |
| 7667 | maize | ubiquitin | — | — | Cytoplasm | — | GFP (native) | nos | Jellyfish structural gene |
| 7921 | maize | ubiquitin | — | — | Cytoplasm | — | GFPm | pinII | Cytoplasmic expression |
| 8489 | maize | ubiquitin | — | — | Cytoplasm | — | GFPm | pinII | MAR flanking cassette |
| 8490 | maize | ubiquitin | — | — | Cytoplasm | — | GFPm~S65T | pinII | MAR flanking cassette, red-shift |
| 8080 | maize | ubiquitin | CTP | — | chloroplast | — | GFPm | pinII | Chloroplast signal sequence, cab-m7 from maize |
| 8087 | maize | CPN60 | CPN60 | — | mitochondria | — | GFPm | pinII | Targeted to mitochondria, signal from maize chaparonin 60 |
| 8144 | maize | ubiquitin | BAA | — | secreted | — | GFPm | pinII | Secreted GFP; signal from barley alpha amylase 1 |
| 8757 | maize | ubiquitin | BAA | BLVT | vacuole | — | GFPm | pinII | Barley lectin vacuole signal seq. on carboxy end of BAA-GFPm |
| 8758 | maize | ubiquitin | BAA | HDEL | endoplasmic reticulum | — | GFPm | pinII | HDEL endoplasmic reticulum signal from maize b-70 |
| 8759 | maize | ubiquitin | BAA | — | vacuole | SVT | GFPm | pinII | Sweet potato sporamin vacuole signal sequence |
| 8882 | maize | ubiquitin | — | SKL | peroxisome | — | GFPm | pinII | Consensus peroxisomal signal sequence at carboxy terminus |
| 8986 | maize | ubiquitin | T7 TAG~NLS~ | — | nucleus | — | GFPm | pinII | Nuclear localization sequence |
| 9053 | maize | ubiquitin | T7 TAG~NLS~ | — | nucleus | — | MALS~GFPm | pinII | Nuclear localization sequence; protein fusion to prevent escape |
| 9057 | maize | ubiquitin | — | — | nucleus | — | MALS~GFPm | pinII | Fusion protein to test effect on GFP as reporter |
| 9058 | maize | ubiquitin | — | — | cytoplasm | — | PATm~GFPm | pinII | PAT~GFP fusion to test efficacy |
| 8744 | maize | ubiquitin | — | — | nucleus | — | GFPm~ZmRAD51 | pinII | Protein fusion: for studies on Rad51 expression/function |
| 8081 | maize | ubiquitin | — | — | cytoplasm | FRT | GFPm | pinII | To verify that FRT sequence does not impair expression |
| 8674 | maize | 2x35s | — | — | cytoplasm | O' Adh1 intron | FRT~bar~ FRT~GFPm | pinII | Select on bialaphos, then excise bar and activate GFP |
| 8911 | maize | ubiquitin/ 2x35s | — | adh1 intron I | cytoplasm | Ds | GFPm bar | pinII pinII | ubi~Ds~ 2x35S::bar::pin~ Ds~GFPm::pinII |
| 8088 | maize | ubiquitin | — | — | cytoplasm | — | GFPm~S65T | pinII | Red-shifted GFPm |
| 8138 | maize | ubiquitin | — | — | cytoplasm | — | GFPm~Red2 | pinII | Red-shifted version #2 F64M, S65G, Q69L |
| 8175 | maize | ubiquitin | — | — | cytoplasm | — | Blue FP | pinII | GFPm~modified Y66H |
| 8007 | maize | 2x35s | | | | | adh1 | pinII | Tandem vector |

TABLE 1-continued

PLASMIDS

| PHP Number | Target Crop | Promoter | Targeting 5' Sequence | Targeting 3' Sequence | Localized To: | Other 5' Sequences | Structural Gene | 3' Sequence | Comments |
|---|---|---|---|---|---|---|---|---|---|
| | | ubiquitin | | | | | intron::bar ubi intron::FLP | pinII | for FLP excision of FRT to activate GFPm |
| 8011 | sunflower | 2x35s ALS | — — | — — | cytoplasm | O' | GFPm NPT-II | pinII pinII | Binary |
| 8491 | sunflower | 2xd35s ALS | — — | — — | cytoplasm | O' | GFPm~S65T NPT-II | pinII pinII | Binary with red-shifter GFP |

The ubiquitin promoter is described in Christensen et al., Plant Mol. Biol. 18: 675–689 (1992). The 4×ERE promoter is described in Klein-Hitpass et al., Cell 46: 1053–1061 (1986). The CPN60; 2×35S and ALS promoters are described in Close P. Ph.D. Dissertation, Iowa State University; Gardner et al., Nucl. Acid Res. 9: 2871–2888 (1981) and PHI patent application Ser. No. 08/409,297, respectively. The Omega prime (O') 5-prime sequence is described by Gallie et al., Nucl. Acids Res. 15: 3257–3273 (1987) while the Adh 1 intron I is described by Dennis et al., Nucl. Acids Res. 12: 3983–3990 (1984). The 3-prime sequence pinII is described in An et al., Plant Cell 1: 115–122 (1989). Structural genes used in the construction of is the vectors include the GFP gene (native jellyfish) described by Prasher et al., Gene 111: 229–233 (1992); the maize ALS gene described by Fromm et al., Bio/Technol. 8: 883 (1990) and the maize HPRG described by Steifel et al., Plant Mol. Biol. 11: 483–493 (1988). The FLP/FRT system contained in plasmids PHP8674 and PHP8007 is described in O'Gorman et al., Science 251: 1351–1355 (1991) and Jayaram M., Proc. Natl. Acad. Sci. USA 82: 5875–5879 (1985). The Ac/Ds system is described by Muller-Neumann et al., Mol. Gen. Genet. 198: 19–24 (1984).

For Agrobacterium-mediated transformation of sunflower, the backbone of PHP8011 is a bin 19-based vector. Beven, Nucl. Acids Res. 12: 8711–8721 (1984). The NPT-II cassette was removed from bin 19 and the following cloned between the left and right border sequences; the double 35S promoter, omega, the GFPm coding sequence and the pinII 3' region (all described above) were cloned downstream of the left border sequence, followed in a head-to-tail orientation by the BnALS3 promoter, the NPT-II coding sequence and the pinII 3' region. Beven, "Binary Agrobacterium Vectors for Plant Transformation", Nucl. Acids Res. 12: 8711–8721 (1984).

GFPr, BFP and GFPs (soluble GFP) were constructed by means of oligonucleotide-directed mutagenesis of the GFPm nucleotide sequence shown in FIG. 1 as described by Ausubel, supra. With regard to GFPr, TCC was changed to ACG resulting in the S65T substitution in the GFP amino acid sequence. With regard to BFP, TAC was changed to CAC, resulting in the Y66H substitution in the GFP amino acid sequence.

With regard to GFPs, the following sequence changes in GFPm were made. TTC was changed to AGC, resulting in a F99S substitution in the GFP amino acid sequence. The oligonucleotide used to introduce this mutation also caused a silent mutation at R96 (AGC changed to CGG), thereby adding a BsrBI restriction site. ATG was changed to ACC, resulting in an M153T substitution in the GFP amino acid sequence GTG was changed to GCC, resulting in a V163A substitution in the GFP amino acid sequence. A single oligonucleotide was used to change the amino acids at 153 and 163. This oligonucleotide also caused a silent mutation at A154 (GCC changed to GCG), which added a SacII restriction site. As reported by Crameri et al., supra, these three amino acid changes did not alter the absorption/ emission characteristics of GFP. These three amino acid substitutions, however, increased the solubility of GFP. Maize cells transformed with the GFPs gene fluoresce in blue to UV light based on transient assays.

EXAMPLE 2

Maize Transformation with GFP Screening or Bialaphos Selection

Maize Hi-II immature embryos were co-transformed via microprojectile bombardment with a mixture of PHP7814 (ubi::PAT::pinII) and PHP8409. Plasmid PHP7814 carries the PAT gene encoding resistance to bialaphos operably linked to the ubiquitin promoter and the terminator from the pinII gene. Standard $CaCl_2$/spermidine precipitation of DNA onto tungsten microprojectiles was used to prepare the DNA-particles. Prior to bombardment, the embryos of approximately 1.5–2.0 mm in length were cultured on 560P medium including N6 salts, Erikkson's vitamins, 0.69 mg/L proline, 2 mg/L 2,4-D, and 31% sucrose. After 4–5 days of incubation in the dark at 28° C., embryos were removed from 560P medium and cultured, coleorhizal end up, on 560L medium which is equivalent to 560P except that it contains 12% sucrose. Embryos were allowed to acclimate to this medium for 3 h prior to transformation.

Embryos were transformed using the PDS-1000 Helium Gun from Bio-Rad at one shot per sample using 650 PSI rupture disks. On average approximately 0.0067 μg of DNA was delivered per shot. For each treatment (pat gene with bialaphos selection or GFP gene with screening for GFP), 447 embryos were used. For the bialaphos-selection treatment; following bombardment, the embryos were maintained on 560L medium for 48 h before transfer to 560R selection medium containing N6 salts, Erikkson's vitamins, 2 mg/L 2,4-D, 3% sucrose and 3 mg/L bialaphos. Plates were maintained at 28° C. in the dark and were observed for colony recovery. Transfer of colonies to fresh medium occurred every two weeks. Transgenic colony recovery under bialaphos selection was accomplished by picking the healthy, growing transgenic calli from amongst the inhibited background of non-transgenic tissue as the material was progressively transferred to fresh media. For the GFP screening treatment, 560P media was used after bombardment and the two-day recovery on 560L. Calli were transfered to fresh non-selective 560P medium every two weeks.

Screening for GFP expression was carried out at each transfer using a Xenon and/or Mercury light source with the appropriate filters for GFP visualization.

TABLE 2

Recovery of Transgenic Events in Maize Hi-II Callus Using Either GFP Visualization or Bialaphos Selection

| | Number of Events Recovered | |
|---|---|---|
| Selection Method | Initial Events | Events Capable of Regeneration |
| Bialaphos selection | 16 | 12 |
| Screened using GFP | 9 | 8 |

Transgenic events were recovered from each treatment. The largest number of transgenic events were consistently obtained by means of bialaphos selection. However, the frequency of recovery of transgenic events with GFP screening was approximately one-half the rate of recovery with bialaphos selection which was surprisingly high considering that GFP screening does not rely on selection of transgenic events in the presence of a cellular toxin.

Once GFP expressing colonies were identified they were monitored regularly for new growth and expression using the Xenon light source. Plant cells containing GFP were regenerated by transferring the callus to 288 medium containing MS salts, 1 mg/L IAA, 0.5 mg/L zeatin and 4% sucrose. The callus was placed in the light. As plantlets developed they were transferred to tubes containing 272K, hormone-free MS medium and 3% sucrose. The percentage of green fluorescent colonies that regenerated into whole plants was determined.

Leaf samples were collected from TO transgenic plants from events recovered by means of bialaphos selection, or for events recovered by means of GFP visualization (nonselected). Genomic DNA was extracted from all leaf samples and Southern analysis was performed using the PAT and GFP genes as hybridization probes. Hybridization for the PAT gene and GFP gene were performed sequentially on the same blots, by stripping and reprobing for the other transgene. Bands hybridizing for the PAT gene and for the GFP gene were observed in all 8 GFP-screened events tested and in all 12 of the bialaphos selected events tested. Copy numbers and integration patterns for both treatments appeared similar, and were consistent with previous experiments by the inventors using bialaphos selection of callus. Copy numbers ranged from low (single or two copies for each gene) to numerous (i.e., >5 copies per gene). Integration events were predominantly at single integration sites but in some cases integration at multiple locations in the genome was observed.

Bialaphos is the most efficient chemical selective agent for maize. Consequently, the high frequency with which transgenic events were obtained with GFP screening, compared to bialaphos selection, was unexpected. An advantage of GFP screening over bialaphos selection is that non-transformed tissue is not killed. Accordingly, transgenic sectors containing the GFP gene develop in a healthier environment for growth and development.

EXAMPLE 3

The GFP Marker in Maize Cytoplasm, Chloroplast and Mitochondria

Maize A188×B73-derived cells were transformed with plasmids PHP080, PHP7921 and PHP8087. Each of these plasmids is described in Example 1 and Table 1. Plasmid PHP8080 carries the GFPm gene operably linked to the ubiquitin promoter and a chloroplast signal sequence. GFP is directed to the chloroplasts of cells transformed with PHP8080. Plasmid PHP7921 carries the GFPm gene operably linked to ubiquitin promoter. GFP remains in the cytoplasm of cells transformed with pPGP7921. Plasmid PHP8087 carries the GFPm gene operably lined to the CPN60 promoter and CPN60 signal sequence. GFP is directed to mitochondria of cells transformed with pPGP8087.

The cells were transformed by culturing maize embryos approximately 1.5 to 2 mm in length onto 560P medium containing N6 salts, Erikkson's vitamins, 0.69 g/L Proline, 2 mg/L 2,4-D and 3% sucrose. After 4–5 days of incubation in the dark at 28° C., embryos were removed from 560P medium and cultured, coleorhizal end up, onto 560L medium which is equivalent to 560P but contains 12% sucrose. Embryos were allowed to acclimate to this medium for 3 h prior to transformation. Embryos were transformed using the PDS-1000 Helium Gun from Bio-Rad at one shot per sample using 650PSI rupture disks. DNA delivered per shot averaged at 0.0667 μg. Following bombardment, all embryos were maintained on 560L medium for 48 hours before transfer to 3% sucrose and 3 mg/L bialaphos. Plates were maintained at 28° C. in the dark and were observed for colony recovery with transfers to fresh medium occurring every two weeks. Transgenic colony recovery was noted initially as growing callus tissue with a healthy phenotype on selection. Screening for GFP expression was completed with each transfer using a Xenon light source with UV filter attachments.

GFP localization was confirmed by analysis of TO callus. Samples of calli from the targeted GFP transformations were fixed in FAA and then examined using an inverted microscopes with UV filters to visualize GFP. For each targeted construct GFP expression was localized to the specified organelle.

Once GFP expressing colonies were identified they were monitored regularly for new growth and expression using the Xenon light source. Plant cells containing GFP were regenerated by transferring the callus to 288 medium containing MS salts, 1 mg/L IAA, 0.5 mg/L zeatin and 4 sucrose. The callus was placed in the light. As plantlets developed they were transferred to tubes containing 272K, hormone-free MS medium and 3% sucrose. The percentage of green fluorescent colonies that regenerated into whole plants was determined.

Regeneration of plants from callus transformed with PHP8080, PHP7921, and PHP8087 appeared to vary between constructs; plants were successfully regenerated from independent transformed calli at respective frequencies of 35, 54 and 86%. Transformation was confirmed by Southern blot analyses using both the BAR and GFPm genes as hybridization probes. GFP localization in various subcellular compartments was confirmed in stable transgenic maize cells using epifluorescent microscopy and image enhancement software.

TABLE 3

Regeneration Frequency Of Maize Transformed With GFP
Directed to Different Subcellular Compartments

| Exp # | Total Colonies | Green | Regenerate | Percentage | Ave. Plant Event |
|---|---|---|---|---|---|
| Chloroplast | | | | | |
| ..4.01 | 32 | 23 | 4 | 17 | 6 |
| ..4.03 | 0 | — | — | — | — |
| ..4.06 | 13 | 11 | 8 | 73 | 3 |
| Totals | 45 | 34 | 12 | 35* | |
| Cytoplasm | | | | | |
| ..4.01 | 7 | 6 | 2 | 33 | 4 |
| ..4.03 | 7 | 5 | 4 | 80 | 5 |
| ..4.06 | 8 | 7 | 6 | 86 | 4 |
| ..4.08 | 9 | 9 | 3 | 33 | 2 |
| ..4.11 | 3 | 3 | 1 | 33 | 4 |
| Totals | 34 | 30 | 16 | 54* | |
| Mitochondrial | | | | | |
| ..4.03 | 5 | 3 | 1 | 33 | 9 |
| ..4.06 | 13 | 11 | 11 | 100 | 4 |
| Totals | 18 | 14 | 12 | 86* | |

*This is not a mean regeneration frequency, but instead is calculated from the totals for all treatments.

Transformed plants containing GFP in the mitochondrial subcellular compartment grew more vigorously than plants containing GFP in the cytoplasm or chloroplast. The transformed plants containing GFP in the mitochondria were equivalent to the controls in terms of growth rate and appearance.

In contrast, transformed plants containing GFP in the chloroplast were difficult to regenerate. This callus produced a preponderance of roots with few shoots. Almost all the plants containing GFP in the chloroplast that were regenerated and reached maturity clearly exhibited stress with narrow and somewhat flaccid leaves, reduced stature, yellow leaves (presumably caused by reduced chlorophyll levels) and male sterility.

Germination of T1 embryos have been tested in the following manner. Aliquots of seed from a number of independent transformants were imbibed and the embryos were excised and placed on hormone-free MS medium with 30% sucrose for germination (this in vitro test made it easier to visualize the seedling). All embryos were germinated in the dark and then scored for visual GFP expression using UV-blue excitation under the dissecting microscope.

For each event tested aliquots of 5 or 10 seeds/event were imbibed, excised and scored for germination and fluorescence. The germination frequency for excised progeny produced on-plants transformed with PHP7921 and PHP8080 was good. The germination frequency for excised progeny produced on plants transformed with PHP8087 was good for 2 events (10/10), low for one event (2/10). No detectable germination was observed for 2 events. This lowered germination frequency could be due to mitochondrially-expressed GFP expression per se, but it could also be the result of event-to-event variation sometimes observed in transgenic lines.

Germination of a single event from plants transformed with PHP7921 was tested differently. Seed were screened using a UV-blue light source, and 10 seed with GFP-expressing seed (embryos and endosperm) were selected. Five of these seed were planted in soil, and in the other 5 the embryos were excised and germinated on medium. None of the seed in soil germinated, while all excised embryos germinated, grew and the seedlings continued to fluoresce. For events where germination appears to be negatively impacted, this could be due to increased GFP concentrations during seed maturation and dry-down. High GFP concentrations and aggregation of the protein has been found to be toxic in E. coli. Crameri et al., Nature Biotechnol. 14: 315–319 (1995).

TABLE 4

T1 Progeny Analysis
Plant Germination and GFPm Expression

| Plasmid | Event Tested | # of T1 Seed Tested | # of T1 Seed Germinated Per Event | # of T1 Plants Expressing GFPm |
|---|---|---|---|---|
| PHP8087: CPN60::mit-GFPm-PinII | 1 | 10 | 0 | 0 |
| PHP8087: CPN60::mit-GFPm-PinII | 2 | 10 | 0 | 0 |
| PHP8087: CPN60::mit-GFPm-PinII | 3 | 10 | 10 | 1 |
| PHP8087: CPN60::mit-GFPm-PinII | 4 | 10 | 2 | 0 |
| PHP8087: CPN60::mit-GFPm-PinII | 5 | 10 | 10 | 2 |
| PHP7921: Ubi::Ubi intron-GFPm-PinII | 1 | 10 | 10 | 4 |
| PHP8080: Ubi::Ubi intron-CTP-GFPm-PinII | 1 | 5 | 5 | 0 |
| PHP8080: Ubi::Ubi intron-CTP-GFPm-PinII | 2 | 5 | 4 | 0 |
| PHP8080: Ubi::Ubi intron-CTP-GFPm-PinII | 3 | 5 | 4 | 0 |
| PHP4810: Ubi::Ubi intron-BAR-PinII | 1 | 5 | 5 | 0 |
| *PHP7921: Ubi::Ubi intron-GFPm-PinII | 2 | 10 5 germinated in vitro and 5 germinated in soil | 5 Germination occurred only from in vitro cultures | 5 Seed planted in soil also were GFPM+ |

*For all seed except those designated in the PHP7921 transformation, embryos were excised from imbibed seed and germinated on MS medium containing no hormones and 3% sucrose. All embryos were germinated in the dark to allow for visualization of GFPm expression. One event from PHP7921 was tested by planting one half of the seed in soil and one half with embryos from endosperm with culture in vitro. All seed planted in soil did not germinate. The germination rate for embryos excised from the endosperm and cultured in vitro was 100%. All plants expressed GFPm.

EXAMPLE 4

Sunflower Transformation with GFP Screening,
GUS Screening and Kanamycin Selection Experiments were undertaken to test GFP, GUS and NPTII as marker genes for sunflower transformation. Two different kinds of meristem systems (split meristem; intact meristem) and two different kinds of particle systems (FG, focusing gun: He, helium gun) were used. The screenable markers GFP and GUS were tested with the intact meristem system under conditions involving no chemical selection but rather selection of transformants based on visual (GFP) or assayable (GUS) expression in transformed sectors. The NPTII marker gene was tested with the split meristem method using kanamycin for chemical selection of transformants and assays for NPTII expression to identify transformed sectors. In some cases, the experiments were carried only so far as identifying transformed sectors while other experiments were carried out all the way through to test for seed transmission of the marker gene to progeny. Transmission to progeny was confirmed by NPTII ELISA.

Regardless of the exact meristem system or type of particle gun used, the basic transformation protocol involved a combination of wounding by particle bombardment, followed by use of Agrobacterium for DNA delivery, as described by Bidney et al., *Plant Mol. Biol.* 18: 301–313 (1992). The plasmids used for plant transformation in these experiments were PHP167 containing GUS as the screenable marker, PHP8011 containing GFP as the screenable marker as well as the NPTII gene, and PHP762 containing NPTII as the selectable marker. Both PHP167 and PHP762 are binary vectors derived from pGA473. See An et al., *EMBO J.* 4: 277–284 (1985). The binary backbone for PHP8011 is bin 19. See Bevan, *NAR* 12: 8711–8721 (1984).

Procedures for preparation of Agrobacterium and preparation of particles for all of the experiments are described in Bidney et al., supra. The Pioneer sunflower line SMF3 was used in all experiments. See Burrus et al., *Plant Cell Rep.* 10: 161–166 (1991) for information concerning SMF3. The Agrobacterium strain EHA101 is described in Bidney et al. supra and strain EHA105 is described in Hood et al., *Transgen. Res.* 2: 208–218 (1993). Procedures for use of the helium gun, intact meristem preparation, tissue culture and co-cultivation conditions, and transgenic plant recovery for the intact meristem experiments are also described in Bidney et al., supra. Procedures for the use of the focusing gun, i.e., as in the intact meristem experiments, are described in Sautter et al., *Bio/Technol.* 9: 1080–1085 (1991). Procedures for use of the helium gun, split meristem preparation, tissue culture, co-cultivation, kanamycin selection and transgenic plant recovery for the split meristem experiments are described in Malone-Schoneberg et al., *Plant Sci.* 103: 199–207 (1994).

Parameters and general use of the focusing gun were similar to those 1.4 μm described in Sautter et al., supra. Gold particles measuring at a concentration of $0.5\times10^6$/μl and 80 bars of nitrogen were typically used although different sized particles (0.25 to 2.5 μm) and different nitrogen pressures (40–160 bar) were tested. For the Dupont PDS-1000 helium driven particle bombardment device, the meristems were bombarded twice at the highest shelf with 600 psi rupture discs and a vacuum of 26 inches Hg and 1.8 μm tungsten particles. The intact meristem transformation method involved imbibing seed for 24 hours in the dark, removing the cotyledons and root radical, followed by culturing of the meristem explants. Twenty-four hours later, the primary leaves were removed to expose the apical meristem. The explants were placed apical dome side up and bombarded twice with particles, followed by co-cultivation with Agrobacterium. To start the co-cultivation for intact meristems a 0.5 μl droplet of $OD^{600}$ 4.0 Agrobacterium was placed on the meristem. After a 3-day co-cultivation the meristems were transferred to culture medium with 250 μg/ml cefotaxime (+100 mg/l kanamycin for the NPTII selection experiments). Selection has also been done using so gm/l kanamycin. The split meristem method involved imbibing seed, breaking of the cotyledons to produce a clean fracture at the plane of the embryonic axis, excising the root tip and then bisecting the explants longitudinally between the primordial leaves. The two halves were placed cut surface up on the medium then bombarded twice with particles, followed by co-cultivation with Agrobacterium. For split meristems, after bombardment the meristems were placed in an $OD^{600}$ 0.6 Agrobacterium suspension for 30 minutes. They were then removed from the suspension onto solid culture medium for 3-day co-cultivation. After this period, the meristems were transferred to fresh medium with 250 μg/ml cefotaxime (+100 mg/l kanamycin for selection) Selection has also been done using 50 gm/l kanamycin.

Table 5 summarizes the results from experiments looking at the frequency of transformed sectors in primary shoots and secondary branches. Table 6 summarizes the results from experiments carried through to progeny for analysis of seed transmission. Transformants were identified in either seed or plants by assaying for marker gene expression. For GUS expression, activity was determined using either histochemical staining or the fluorometric assay, see Jefferson et al., *EMBO J.* 6: 3901–3907 (1987). Inheritance of transgene expression was assessed using an NPTII ELISA.

TABLE 5

Overall Transformed Sector Frequencies for Sunflower Transformation

| MARKER | PLASMID PHP # | GUN | MERISTEM PREPARATION | AVE. % SECTORS | REPS (N) |
|---|---|---|---|---|---|
| Screening: | | | | | |
| GUS | 167 | FG | Intact | 22.0 | 15 |
| GUS | 167 | FG | Intact | 15.0 | 3 |
| GUS | 167 | He | Intact | 13.6 | 12 |
| GFP | 8011 | He | Intact | 7.5 | 1 |
| Selection: | | | | | |
| NPTII/Kan | 762 | FG | Intact | 12.7 | 3 |

TABLE 6

Overall Sector and Seed Transmission for Sunflower Transformation

| MARKER | PLASMID PHP # | GUN | MERISTEM PREPARATION | AVE. % SECTORS | REPS (N) | SEED TRANSMISSION |
|---|---|---|---|---|---|---|
| Screening: | | | | | | |
| GUS | 167 | FG | Intact | 15.0 | 3 | 0/8 |
| GFP | 8011 | He | Intact | 7.5 | 1 | 9/10 |
| Selection: | | | | | | |
| NPTII/KAN | 762 | FG | Intact | 12.7 | 4 | 0/2 |
| NPTII/KAN | 8011 | He | Split | 1.8 | 4 | 6/8 |

For evaluation of initial sector frequencies, GUS seemed to be the most effective marker gene (Tables 5 and 6). However, based on screening alone (no selection) the observed GUS sectors did not subsequently contribute to the germline and thus did not transmit to progeny (Table 6). It was unlikely that this was due to the use of the focusing gun because, both quantitatively and qualitatively, mapping of GUS sectors after use of each type of gun was comparable. GFP was significantly better than NPTII (7.5% vs. 1.8%, see Table 6) for both sector frequency and seed transmission when compared using the helium gun. Progeny from GFP-expressing (no chemical selection but instead visually selecting using GFP) TO plants were analyzed for NPTII expression (Table 6) Progeny from 10 plants were tested and 9 showed inheritance of NPTII activity. From kanamycin-selected TO plants, 6 out of 8 tested showed transmission of NPTII expression to the progeny. Not only has GFP "visual selection" worked unexpectedly well for recovering the primary transformants (i.e. compare Tables 3 and 4), but cotransformation and inheritance of transgene expression was also very efficient.

TABLE 7

Progeny Analysis of Transformation Experiments of SMF3 with GFP (PHP8011: CaMV-GFPm, ALS-NPTII)

| Treatment (Comments) | SID | No. of Seeds Screened | TO NPTII Map Range | Maximum NPTII | Transmission Efficiency |
|---|---|---|---|---|---|
| Topdown | 281976 | 246 | 12.6->30 | 9.9 | 9/10 |
| Non-selected | 281977 | 139 | 16.3-> | 11.9 | |
| (from 1 experi- | 281978 | 127 | >30 | >30 | |
| ment, 120 ex- | 281979 | 175 | 9–27 | 6 | |
| plants in total) | 281980 | 74 | >30 | 4 | |
| | 281983 | 15 | 3–21.3 | 6.5 | |
| | 319454 | 124 | 4.1–18.7 | 5.9 | |
| | 319453 | 118 | ++ | 8.6 | |
| | 281982 | 47 | >30 | 6.2 | |
| | 281981 | 3 | >30 | 0 | |
| Split selected | 248112 | 6 | ++ | 2.3 | 6/8 |
| (from 4 experi- | 248113 | 24 | >30 | 7.8 | |
| ments, 955 ex- | 248111 | 41 | >30 | >30 | |
| plants in total) | 248107 | 23 | 17 | 2.7 | |
| | 248114 | 67 | >30 | 1.2 | |
| | 248110 | 8 | 4.1 | 0 | |
| | 248109 | 6 | 10.7 | 0 | |
| | 248115 | 86 | ++ | 5.5 | |

Parallel experiments comparing GFP screening, GUS screening and NPTII/kanamycin selection can be performed using intact meristems, the Agrobacterium strain ERA105 and the helium gun, in side-by-side comparisons. Plasmid PHP8011 can be used for GFP/NPII comparisons. An identical plasmid substituting the GUS structural gene for GFP can be used for GUS/NPTII comparisons, and both plasmids can be used in side-by-side experiments for GUS/GFP comparisons. Sector frequency in primary shoots and secondary shoots can be assayed and calculated as described above. Inheritance and expression of transgenes can also be analyzed in these experiments.

EXAMPLE 5

GFP as a FLP-Mediated Excision Marker in Maize

Immature embryos of the Hi-II genotype were bombarded with PHP8674 which contains a GFPm reporter gene that is activated upon FLP recombinase-mediated FRT excision. Plasmid PHP8674 also carries a constitutively expressed gene for bialaphos resistance. Stably transformed callus was selected on bialaphos and examined under UV-blue light for GFP expression. No GFP expression was observed in these primary transformants. Pieces of callus transformed with PHP8674 were then bombarded with PHP8007. Plasmid PHP8007 contains the FLP recombinase gene operably linked to the ubiquitin promoter. Callus sectors expressing GFP were first observed ten days after the second bombardment. These GFP-expressing sectors continued to grow and express the transgene after one month of culture. As a negative control the FRT/GFPm stably transformed callus was also bombarded with a non-FLP containing plasmid. This treatment did not produce GFP expressing sectors.

As a second control for this experiment the consecutive treatments were, done in opposite order. Hi-II immature embryos were bombarded with PHP8007 which carries the FLP recombinase gene and a bialaphos resistance gene. Stable transformants were recovered following selection on medium containing bialaphos. These calli were re-bombarded with PHP8674. GFP expression was observed in the callus but this faded over 5–10 days until it could no longer be detected. The stably transformed callus-expresses FLP recombinase. Introduction of PHP8674 likely provided the substrate for excision (the FRT sites along with spacer DNA between the sites) which activated the GFP cassette while still on the plasmid. This "activated expression" was only transient and disappeared as the plasmid was degraded.

EXAMPLE 6

GFP Targeting to the Nucleus as a Fusion Protein

Plasmid PHP9053 was constructed in which the GFP protein was fused to the ALS enzyme (designated MALS for maize-ALS). The ALS gene, which encodes a protein normally found in the cytoplasm, is typically used to confer herbicide resistance. Fang et al., *Plant Mol. Biol.* 18: 1185–1187 (1992). A nuclear localization signal from simian virus 40 was fused to the N terminus of GFPm as described in Example 1 (Kalderon et al., *Cell* 39: 499–509 (1984) with the ALS enzyme fused to the C terminus. The sequence encoding this nuclear targeted fusion protein (in construct PHP9053) was introduced into maize cells using particle bombardment as described previously. Once gene expression was confirmed through GFP fluorescence under the microscope, tissue was fixed as described earlier and examined to determine subcellular localization of GFP. Fluorescence was localized to the nucleus. Plant regeneration and assessment of toxicity for this experiment has not yet been done.

GFP was targeted to the nucleus by fusing the protein to another polypeptide that is normally compartmentalized in the nucleus. For example, the GFPZm-RAD51 fusion found in plasmid PHP8744 contains RAD51, a protein required for mitotic and meiotic recombination and double-stranded break repair, fused to GFP. The gene encoding RAD51 was cloned from yeast. Haaf et al., *Proc. Nat Acad. Sci.* 92: 2298–2302 (1995). Degenerate primers based on the nucleotide sequence of the RAD51 gene cloned from yeast were used to identify and isolate clones containing the RAD51 gene from maize. The carboxy terminus of GFPm was fused to the amino terminus of ZmRAD51a. Maize cells were transformed with the GFPm-ZmRAD51 fusion and fluorescence was localized in the nucleus. Plant regeneration and assessment of toxicity for this experiment has not yet been done.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

SEQUENCE LISTING

<160> NUMBER OF SEQ ID NOS: 24

<210> SEQ ID NO 1
<211> LENGTH: 717
<212> TYPE: DNA
<213> ORGANISM: Artificial Sequence
<220> FEATURE:
<223> OTHER INFORMATION: Description of Artificial Sequence: Synthetic
      DNA encoding GFP
<221> NAME/KEY: CDS
<222> LOCATION: (1)..(714)

<400> SEQUENCE: 1

```
atg tcc aag ggc gag gag ctc ttc acc ggc gtg gtg ccc atc ctc gtg       48
Met Ser Lys Gly Glu Glu Leu Phe Thr Gly Val Val Pro Ile Leu Val
 1               5                  10                  15 gag ctc gac ggc gac gtg aac ggc cac aag ttc tcc gtg tcc ggc gag       96
Glu Leu Asp Gly Asp Val Asn Gly His Lys Phe Ser Val Ser Gly Glu
             20                  25                  30 ggc gag ggc gac gcc acc tac ggc aag ctc acc ctc aag ttc atc tgc      144
Gly Glu Gly Asp Ala Thr Tyr Gly Lys Leu Thr Leu Lys Phe Ile Cys
         35                  40                  45 acc acc ggc aag ctc ccc gtg ccc tgg ccc acc ctc gtg acc acc ttc      192
Thr Thr Gly Lys Leu Pro Val Pro Trp Pro Thr Leu Val Thr Thr Phe
 50                  55                  60 tcc tac ggc gtg cag tgc ttc tcc agg tac ccc gac cac atg aag cag      240
Ser Tyr Gly Val Gln Cys Phe Ser Arg Tyr Pro Asp His Met Lys Gln
 65                  70                  75                  80 cac gac ttc ttc aag tca gcc atg ccc gag ggc tac gtg cag gag agg      288
His Asp Phe Phe Lys Ser Ala Met Pro Glu Gly Tyr Val Gln Glu Arg
                 85                  90                  95 acc atc ttc ttc aag gac gac ggc aac tac aag acc agg gcc gag gtg      336
Thr Ile Phe Phe Lys Asp Asp Gly Asn Tyr Lys Thr Arg Ala Glu Val
            100                 105                 110 aag ttc gaa ggc gac acc ctc gtg aac agg att gag ctc aag ggc atc      384
Lys Phe Glu Gly Asp Thr Leu Val Asn Arg Ile Glu Leu Lys Gly Ile
        115                 120                 125 gac ttc aag gag gac ggc aac atc ctc ggc cac aag ctc gag tac aac      432
Asp Phe Lys Glu Asp Gly Asn Ile Leu Gly His Lys Leu Glu Tyr Asn
130                 135                 140 tac aac tcc cac aac gtg tac atc atg gcc gac aag cag aag aac ggc      480
Tyr Asn Ser His Asn Val Tyr Ile Met Ala Asp Lys Gln Lys Asn Gly
145                 150                 155                 160 atc aag gtg aac ttc aag atc agg cac aac atc gag gac ggc tca gtg      528
Ile Lys Val Asn Phe Lys Ile Arg His Asn Ile Glu Asp Gly Ser Val
                165                 170                 175 cag ctc gct gac cac tac cag cag aac acc ccc atc ggc gac ggc ccc      576
Gln Leu Ala Asp His Tyr Gln Gln Asn Thr Pro Ile Gly Asp Gly Pro
            180                 185                 190 gtg ctc ctc ccc gac aac cac tac ctc tcc acc cag tcc gcc ctc tcc      624
Val Leu Leu Pro Asp Asn His Tyr Leu Ser Thr Gln Ser Ala Leu Ser
        195                 200                 205 aag gac ccc aac gag aag agg gac cac atg gtg ctc ctc gag ttc gtg      672
Lys Asp Pro Asn Glu Lys Arg Asp His Met Val Leu Leu Glu Phe Val
    210                 215                 220 acc gct gct ggc atc acc cac ggc atg gac gag ctc tac aag tga          717
Thr Ala Ala Gly Ile Thr His Gly Met Asp Glu Leu Tyr Lys
225                 230                 235
```

<210> SEQ ID NO 2

-continued

```
<211> LENGTH: 238
<212> TYPE: PRT
<213> ORGANISM: Artificial Sequence
<220> FEATURE:
<223> OTHER INFORMATION: Description of Artificial Sequence: Synthetic
      GFP

<400> SEQUENCE: 2

Met Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 3
<211> LENGTH: 159
<212> TYPE: DNA
<213> ORGANISM: Maize sp.
<220> FEATURE:
<221> NAME/KEY: CDS
<222> LOCATION: (1)..(159)

<400> SEQUENCE: 3 atg gcg tcc tcc acg atg gcc ctc tcc tcc acc gcc ttc gcc ggc aag       48
Met Ala Ser Ser Thr Met Ala Leu Ser Ser Thr Ala Phe Ala Gly Lys
  1               5                  10                  15 gcc gtg aac gtg ccg tcg tcg tcc gcc ttc gag gcc cgc gtg acc atg       96
Ala Val Asn Val Pro Ser Ser Ser Ala Phe Glu Ala Arg Val Thr Met
             20                  25                  30 agg aag acg gcg gcg aag gcc aag cca gct gcg gcg tcc ggg agc ccg      144
Arg Lys Thr Ala Ala Lys Ala Lys Pro Ala Ala Ala Ser Gly Ser Pro
         35                  40                  45 tgg tac ggc ccc atg                                                  159
Trp Tyr Gly Pro Met
```

-continued

```
<210> SEQ ID NO 4
<211> LENGTH: 53
<212> TYPE: PRT
<213> ORGANISM: Maize sp.

<400> SEQUENCE: 4

Met Ala Ser Ser Thr Met Ala Leu Ser Ser Thr Ala Phe Ala Gly Lys
 1               5                  10                  15
Ala Val Asn Val Pro Ser Ser Ser Ala Phe Glu Ala Arg Val Thr Met
             20                  25                  30
Arg Lys Thr Ala Ala Lys Ala Lys Pro Ala Ala Ala Ser Gly Ser Pro
         35                  40                  45
Trp Tyr Gly Pro Met
     50

<210> SEQ ID NO 5
<211> LENGTH: 537
<212> TYPE: DNA
<213> ORGANISM: Maize sp.
<220> FEATURE:
<221> NAME/KEY: CDS
<222> LOCATION: (1..69, 496..537)

<400> SEQUENCE: 5 atg tac cgc gcg gcc gct agc ctc gcc tcc aag gcg cgg caa gcc ggg      48
Met Tyr Arg Ala Ala Ala Ser Leu Ala Ser Lys Ala Arg Gln Ala Gly
 1               5                  10                  15 agc agc tcc gcc gct cgc cag gtgagagcag actcgtgttt atacgcgtgt         99
Ser Ser Ser Ala Ala Arg Gln
             20 gatgggtctg atggaggatc ccgccctcag atttggtaat gttggcctgg ggttctagta   159 gttctgcgtg cagggctgtg ggtttgctgc atggtgctgt ttattttggt ggcgatctgc   219 cggaatctgt agttcgctcg cgcaaaatct aagctagctc gctaatggcg tactggcgtg   279 gggtttcaca ttaatctacg gtggtgaact cgtcactacc gtcctccagt tagctgttag   339 acaccgaata cactgattgg cagttgagaa acattgatct gatccagcag aaatcgatgt   399 cttgtgaaat tcgttatttt attgtcgtgt aaccttgggg catggcagtc tctaattgat   459 cacgcactca cctctgttgt gtgtgatgct ttatag gtt gga agc agg ctt gcc     513
                                        Val Gly Ser Arg Leu Ala
                                                         25 tgg agc agg aac tat gct gcc atg                                     537
Trp Ser Arg Asn Tyr Ala Ala Met
 30                  35

<210> SEQ ID NO 6
<211> LENGTH: 37
<212> TYPE: PRT
<213> ORGANISM: Maize sp.

<400> SEQUENCE: 6

Met Tyr Arg Ala Ala Ala Ser Leu Ala Ser Lys Ala Arg Gln Ala Gly
 1               5                  10                  15
Ser Ser Ser Ala Ala Arg Gln Val Gly Ser Arg Leu Ala Trp Ser Arg
             20                  25                  30
Asn Tyr Ala Ala Met
         35
```

<210> SEQ ID NO 7
<211> LENGTH: 78
<212> TYPE: DNA
<213> ORGANISM: Hordeum vulgare
<220> FEATURE:
<221> NAME/KEY: CDS
<222> LOCATION: (1)..(78)

<400> SEQUENCE: 7

```
atg gcc aac aag cac ctg agc ctc tcc ctc ttc ctc gtg ctc ctc ggc     48
Met Ala Asn Lys His Leu Ser Leu Ser Leu Phe Leu Val Leu Leu Gly
 1               5                  10                  15 ctc tcc gcc tcc ctc gcc tcc gga tcc atg                              78
Leu Ser Ala Ser Leu Ala Ser Gly Ser Met
            20                  25
```

<210> SEQ ID NO 8
<211> LENGTH: 26
<212> TYPE: PRT
<213> ORGANISM: Hordeum vulgare

<400> SEQUENCE: 8

```
Met Ala Asn Lys His Leu Ser Leu Ser Leu Phe Leu Val Leu Leu Gly
 1               5                  10                  15

Leu Ser Ala Ser Leu Ala Ser Gly Ser Met
            20                  25
```

<210> SEQ ID NO 9
<211> LENGTH: 54
<212> TYPE: DNA
<213> ORGANISM: Hordeum vulgare
<220> FEATURE:
<221> NAME/KEY: CDS
<222> LOCATION: (1)..(54)

<400> SEQUENCE: 9

```
aag atc tac gtg ttc gcc gag gcc atc gcc gcc aac tcc acc ctc gtg     48
Lys Ile Tyr Val Phe Ala Glu Ala Ile Ala Ala Asn Ser Thr Leu Val
 1               5                  10                  15 gcc gag                                                              54
Ala Glu
```

<210> SEQ ID NO 10
<211> LENGTH: 18
<212> TYPE: PRT
<213> ORGANISM: Hordeum vulgare

<400> SEQUENCE: 10

```
Lys Ile Tyr Val Phe Ala Glu Ala Ile Ala Ala Asn Ser Thr Leu Val
 1               5                  10                  15

Ala Glu
```

<210> SEQ ID NO 11
<211> LENGTH: 42
<212> TYPE: DNA
<213> ORGANISM: Maize sp.
<220> FEATURE:
<221> NAME/KEY: CDS
<222> LOCATION: (1)..(42)

<400> SEQUENCE: 11

```
aag atc tac gac ggc ggc gtg gac gac gac cac gac gag ctc              42
Lys Ile Tyr Asp Gly Gly Val Asp Asp Asp His Asp Glu Leu
 1               5                  10
```

```
<210> SEQ ID NO 12
<211> LENGTH: 14
<212> TYPE: PRT
<213> ORGANISM: Maize sp.

<400> SEQUENCE: 12

Lys Ile Tyr Asp Gly Gly Val Asp Asp Asp His Asp Glu Leu
 1               5                  10

<210> SEQ ID NO 13
<211> LENGTH: 141
<212> TYPE: DNA
<213> ORGANISM: Ipomoea batatas
<220> FEATURE:
<221> NAME/KEY: CDS
<222> LOCATION: (1)..(141)

<400> SEQUENCE: 13 atg gcc aac aag cac ctg agc ctc tcc ctc ttc ctc gtg ctc ctc ggc      48
Met Ala Asn Lys His Leu Ser Leu Ser Leu Phe Leu Val Leu Leu Gly
 1               5                  10                  15 ctc tcc gcc tcc ctc gcc tcc gga cac agc agg ttc aac ccc atc agg      96
Leu Ser Ala Ser Leu Ala Ser Gly His Ser Arg Phe Asn Pro Ile Arg
             20                  25                  30 ctg ccc acc acc cac gag ccc gcc agc agc gag acc gga tcc atg         141
Leu Pro Thr Thr His Glu Pro Ala Ser Ser Glu Thr Gly Ser Met
         35                  40                  45

<210> SEQ ID NO 14
<211> LENGTH: 47
<212> TYPE: PRT
<213> ORGANISM: Ipomoea batatas

<400> SEQUENCE: 14

Met Ala Asn Lys His Leu Ser Leu Ser Leu Phe Leu Val Leu Leu Gly
 1               5                  10                  15

Leu Ser Ala Ser Leu Ala Ser Gly His Ser Arg Phe Asn Pro Ile Arg
             20                  25                  30

Leu Pro Thr Thr His Glu Pro Ala Ser Ser Glu Thr Gly Ser Met
         35                  40                  45

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: consensus
      peroxisome signal sequence
<221> NAME/KEY: CDS
<222> LOCATION: (1)..(12)

<400> SEQUENCE: 15 aag tcg aag ctt                                                      12
Lys Ser Lys Leu
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: consensus
      peroxisome signal sequence

<400> SEQUENCE: 16

Lys Ser Lys Leu
```

-continued

```
<210> SEQ ID NO 17
<211> LENGTH: 2063
<212> TYPE: DNA
<213> ORGANISM: Pisum sativum
<220> FEATURE:
<221> NAME/KEY: CDS
<222> LOCATION: (52)..(1740)

<400> SEQUENCE: 17
cttgtattac tccaccgaga tatccggatt atcaaggtgg ttggttacta a gca cca      57
                                                        Ala Pro
                                                          1 ccg gga aca gag agg gaa act cta atg aac caa gca atg gct act cca     105
Pro Gly Thr Glu Arg Glu Thr Leu Met Asn Gln Ala Met Ala Thr Pro
      5                  10                  15 ctt tct ctc tct tgt tgt tct cca act cta act cgc agc act ctc ttc    153
Leu Ser Leu Ser Cys Cys Ser Pro Thr Leu Thr Arg Ser Thr Leu Phe
 20                  25                  30 ttc acc aaa acc ttt cca ttt tct cgc tcc ttc tct aca cct ctc cct    201
Phe Thr Lys Thr Phe Pro Phe Ser Arg Ser Phe Ser Thr Pro Leu Pro
 35                  40                  45                  50 ctc tcc acc aaa acc cta att tcc ctc tct cca ccc cat cgc acc ttc    249
Leu Ser Thr Lys Thr Leu Ile Ser Leu Ser Pro Pro His Arg Thr Phe
              55                  60                  65 gcc gtc cgc gct gaa tcc caa aac ggc gcc gac ccc gcc cgc cag tat    297
Ala Val Arg Ala Glu Ser Gln Asn Gly Ala Asp Pro Ala Arg Gln Tyr
          70                  75                  80 gac ttc gac ctt ttc acc atc ggc gct gga agc gga ggc gtc cgt gct    345
Asp Phe Asp Leu Phe Thr Ile Gly Ala Gly Ser Gly Gly Val Arg Ala
      85                  90                  95 tcc cgc ttt gcc tcc aat ttc ggc gct tct tct gct gtc tgc gag ctc    393
Ser Arg Phe Ala Ser Asn Phe Gly Ala Ser Ser Ala Val Cys Glu Leu
100                 105                 110 cct ttc tct act atc tcc tcc gat acc acc ggt ggt gtc ggc ggc acc    441
Pro Phe Ser Thr Ile Ser Ser Asp Thr Thr Gly Gly Val Gly Gly Thr
115                 120                 125                 130 tgt gta ata cgg gga tgt gtc cct aag aaa ttg cta gtc tat gcc tca    489
Cys Val Ile Arg Gly Cys Val Pro Lys Lys Leu Leu Val Tyr Ala Ser
              135                 140                 145 aaa ttc tct cat gaa ttt gaa gaa agc aat ggt ttt gga tgg aga tat    537
Lys Phe Ser His Glu Phe Glu Glu Ser Asn Gly Phe Gly Trp Arg Tyr
          150                 155                 160 gac agt gaa cct aag cat gac tgg agt agt ttg att gct aat aaa aac    585
Asp Ser Glu Pro Lys His Asp Trp Ser Ser Leu Ile Ala Asn Lys Asn
      165                 170                 175 gcc gag ttg cag cgg ctt act ggt atc tat aag aat act ttg aaa aat    633
Ala Glu Leu Gln Arg Leu Thr Gly Ile Tyr Lys Asn Thr Leu Lys Asn
180                 185                 190 gcc ggt gtt aag ttg att gaa ggc cgt gga aag att gta gat gct cac    681
Ala Gly Val Lys Leu Ile Glu Gly Arg Gly Lys Ile Val Asp Ala His
195                 200                 205                 210 aca gtt gat gtt gat ggg aag tta tat tca gcg aaa cac att tta gtt    729
Thr Val Asp Val Asp Gly Lys Leu Tyr Ser Ala Lys His Ile Leu Val
              215                 220                 225 tca gtt gga ggt cga ccc ttc att cct gat att cct gga aag gaa tat    777
Ser Val Gly Gly Arg Pro Phe Ile Pro Asp Ile Pro Gly Lys Glu Tyr
          230                 235                 240 gca ata gat tca gat gct gcc ctt gat tta cca tca aag cct cag aag    825
Ala Ile Asp Ser Asp Ala Ala Leu Asp Leu Pro Ser Lys Pro Gln Lys
```

```
                245                 250                 255
ata gct att gtt ggt ggg ggt tac att gcc ttg gag ttt gct ggt atc      873
Ile Ala Ile Val Gly Gly Gly Tyr Ile Ala Leu Glu Phe Ala Gly Ile
    260                 265                 270 ttt aat ggt ttg aaa agt gaa gtt cat gta ttt ata aga caa aag aag      921
Phe Asn Gly Leu Lys Ser Glu Val His Val Phe Ile Arg Gln Lys Lys
275                 280                 285                 290 gtt ttg cgg gga ttt gat gaa gag att aga gat ttt gtt gca gaa aat      969
Val Leu Arg Gly Phe Asp Glu Glu Ile Arg Asp Phe Val Ala Glu Asn
                295                 300                 305 atg gct ctg aga ggt att gaa ttc cat act gag gag tct cct gta gct     1017
Met Ala Leu Arg Gly Ile Glu Phe His Thr Glu Glu Ser Pro Val Ala
        310                 315                 320 atc act aag gca gct gat ggt tcg ctc tct tta aag acc aac aaa ggt     1065
Ile Thr Lys Ala Ala Asp Gly Ser Leu Ser Leu Lys Thr Asn Lys Gly
    325                 330                 335 act gag gaa ggt ttc tct cat att atg ttt gcc act gga cgc tca cct     1113
Thr Glu Glu Gly Phe Ser His Ile Met Phe Ala Thr Gly Arg Ser Pro
340                 345                 350 aat act aag gat ttg ggc ctg gag tct gtt ggt gtg aaa gtg gct aaa     1161
Asn Thr Lys Asp Leu Gly Leu Glu Ser Val Gly Val Lys Val Ala Lys
355                 360                 365                 370 gat gga tca ata gag gtt gat gaa tac tct caa aca tcg gtt cct tct     1209
Asp Gly Ser Ile Glu Val Asp Glu Tyr Ser Gln Thr Ser Val Pro Ser
                375                 380                 385 att tgg gca att gga gat gct aca aat aga gta aat ctc act cca gtt     1257
Ile Trp Ala Ile Gly Asp Ala Thr Asn Arg Val Asn Leu Thr Pro Val
        390                 395                 400 gct ttg atg gag gga gtg gca tta gca aaa act ttg ttt cag aat gag     1305
Ala Leu Met Glu Gly Val Ala Leu Ala Lys Thr Leu Phe Gln Asn Glu
    405                 410                 415 ccg aca aaa cct gat tat agg gct ata cct tct gct gtg ttt tcc caa     1353
Pro Thr Lys Pro Asp Tyr Arg Ala Ile Pro Ser Ala Val Phe Ser Gln
420                 425                 430 cca cca att gga gga gtt ggt ctt aca gag gaa cag gct gct gaa caa     1401
Pro Pro Ile Gly Gly Val Gly Leu Thr Glu Glu Gln Ala Ala Glu Gln
435                 440                 445                 450 tat ggt gat att gac gtt ttc aca gca aat ttt agg ccg atg aag gcc     1449
Tyr Gly Asp Ile Asp Val Phe Thr Ala Asn Phe Arg Pro Met Lys Ala
                455                 460                 465 acc ctc tct ggg ctt cca gac cgg gtt ttt atg aaa cta ata gtc tct     1497
Thr Leu Ser Gly Leu Pro Asp Arg Val Phe Met Lys Leu Ile Val Ser
        470                 475                 480 gca gaa aca aat gtt gtt ctt gga ttg cac atg tgt gga gaa gat gct     1545
Ala Glu Thr Asn Val Val Leu Gly Leu His Met Cys Gly Glu Asp Ala
    485                 490                 495 gct gaa att gca cag ggg ttt gca gtt ggt att aaa gct gga tta aca     1593
Ala Glu Ile Ala Gln Gly Phe Ala Val Gly Ile Lys Ala Gly Leu Thr
500                 505                 510 aag gcg gac ttt gat gcc aca gta ggc att cat cca act gca gct gag     1641
Lys Ala Asp Phe Asp Ala Thr Val Gly Ile His Pro Thr Ala Ala Glu
515                 520                 525                 530 gaa ttt gtt acc atg agg act ccc act agg aag gtt cga aag aac caa     1689
Glu Phe Val Thr Met Arg Thr Pro Thr Arg Lys Val Arg Lys Asn Gln
                535                 540                 545 gct tca cag ggg aag tca gat tct aaa gca aaa gct gtg gct gga tct     1737
Ala Ser Gln Gly Lys Ser Asp Ser Lys Ala Lys Ala Val Ala Gly Ser
        550                 555                 560 taa gagtattaat ttgcttcaat tattataccc aaagaaactt gctgaggcct          1790
```

-continued

```
taaggcaggt tattgagttt tcgagtgatc tctgtcaacg gagctttcaa gacaattcat    1850
gaaatagcct gcagagctca tctggaaaag gggagcagtg gaattttgcg agctattatg    1910
tgcaatttgt aatttatttc tccttttttt taccaattta tttttcaccc taaccttacc    1970
catttgtaca tattaagatg aaatttcgcg aggtactttg atgttaaata aaataatcta    2030
tcttatgtaa tttgaagcag ttggaactga ggc                                 2063
```

<210> SEQ ID NO 18
<211> LENGTH: 562
<212> TYPE: PRT
<213> ORGANISM: Pisum sativum

<400> SEQUENCE: 18

```
Ala Pro Pro Gly Thr Glu Arg Glu Thr Leu Met Asn Gln Ala Met Ala
 1               5                  10                  15

Thr Pro Leu Ser Leu Ser Cys Cys Ser Pro Thr Leu Thr Arg Ser Thr
            20                  25                  30

Leu Phe Phe Thr Lys Thr Phe Pro Phe Ser Arg Ser Phe Ser Thr Pro
        35                  40                  45

Leu Pro Leu Ser Thr Lys Thr Leu Ile Ser Leu Ser Pro Pro His Arg
    50                  55                  60

Thr Phe Ala Val Arg Ala Glu Ser Gln Asn Gly Ala Asp Pro Ala Arg
65                  70                  75                  80

Gln Tyr Asp Phe Asp Leu Phe Thr Ile Gly Ala Gly Ser Gly Gly Val
                85                  90                  95

Arg Ala Ser Arg Phe Ala Ser Asn Phe Gly Ala Ser Ser Ala Val Cys
            100                 105                 110

Glu Leu Pro Phe Ser Thr Ile Ser Ser Asp Thr Thr Gly Gly Val Gly
        115                 120                 125

Gly Thr Cys Val Ile Arg Gly Cys Val Pro Lys Lys Leu Leu Val Tyr
    130                 135                 140

Ala Ser Lys Phe Ser His Glu Phe Glu Glu Ser Asn Gly Phe Gly Trp
145                 150                 155                 160

Arg Tyr Asp Ser Glu Pro Lys His Asp Trp Ser Ser Leu Ile Ala Asn
                165                 170                 175

Lys Asn Ala Glu Leu Gln Arg Leu Thr Gly Ile Tyr Lys Asn Thr Leu
            180                 185                 190

Lys Asn Ala Gly Val Lys Leu Ile Glu Gly Arg Gly Lys Ile Val Asp
        195                 200                 205

Ala His Thr Val Asp Val Asp Gly Lys Leu Tyr Ser Ala Lys His Ile
    210                 215                 220

Leu Val Ser Val Gly Gly Arg Pro Phe Ile Pro Asp Ile Pro Gly Lys
225                 230                 235                 240

Glu Tyr Ala Ile Asp Ser Asp Ala Ala Leu Asp Leu Pro Ser Lys Pro
                245                 250                 255

Gln Lys Ile Ala Ile Val Gly Gly Gly Tyr Ile Ala Leu Glu Phe Ala
            260                 265                 270

Gly Ile Phe Asn Gly Leu Lys Ser Glu Val His Val Phe Ile Arg Gln
        275                 280                 285

Lys Lys Val Leu Arg Gly Phe Asp Glu Glu Ile Arg Asp Phe Val Ala
    290                 295                 300

Glu Asn Met Ala Leu Arg Gly Ile Glu Phe His Thr Glu Glu Ser Pro
305                 310                 315                 320
```

```
Val Ala Ile Thr Lys Ala Ala Asp Gly Ser Leu Ser Leu Lys Thr Asn
            325                 330                 335
Lys Gly Thr Glu Glu Gly Phe Ser His Ile Met Phe Ala Thr Gly Arg
            340                 345                 350
Ser Pro Asn Thr Lys Asp Leu Gly Leu Glu Ser Val Gly Val Lys Val
            355                 360                 365
Ala Lys Asp Gly Ser Ile Glu Val Asp Glu Tyr Ser Gln Thr Ser Val
            370                 375                 380
Pro Ser Ile Trp Ala Ile Gly Asp Ala Thr Asn Arg Val Asn Leu Thr
385                 390                 395                 400
Pro Val Ala Leu Met Glu Gly Val Ala Leu Ala Lys Thr Leu Phe Gln
            405                 410                 415
Asn Glu Pro Thr Lys Pro Asp Tyr Arg Ala Ile Pro Ser Ala Val Phe
            420                 425                 430
Ser Gln Pro Pro Ile Gly Gly Val Gly Leu Thr Glu Glu Gln Ala Ala
            435                 440                 445
Glu Gln Tyr Gly Asp Ile Asp Val Phe Thr Ala Asn Phe Arg Pro Met
            450                 455                 460
Lys Ala Thr Leu Ser Gly Leu Pro Asp Arg Val Phe Met Lys Leu Ile
465                 470                 475                 480
Val Ser Ala Glu Thr Asn Val Val Leu Gly Leu His Met Cys Gly Glu
            485                 490                 495
Asp Ala Ala Glu Ile Ala Gln Gly Phe Ala Val Gly Ile Lys Ala Gly
            500                 505                 510
Leu Thr Lys Ala Asp Phe Asp Ala Thr Val Gly Ile His Pro Thr Ala
            515                 520                 525
Ala Glu Glu Phe Val Thr Met Arg Thr Pro Thr Arg Lys Val Arg Lys
            530                 535                 540
Asn Gln Ala Ser Gln Gly Lys Ser Asp Ser Lys Ala Lys Ala Val Ala
545                 550                 555                 560
Gly Ser

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: DNA
      encoding the nuclear localization signal from simian virus 40
      (SV40) fused to the N terminus of GFPm
<221> NAME/KEY: CDS
<222> LOCATION: (1)..(42)

<400> SEQUENCE: 19 ccg ccc aag aag aag cgc aag gtg ccc atg aag atc cac atg        42
Pro Pro Lys Lys Lys Arg Lys Val Pro Met Lys Ile His Met
 1               5                  10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: The nuclear
      localization signal from simian virus 40 (SV40) fused to the N
      terminus of GFPm

<400> SEQUENCE: 20

Pro Pro Lys Lys Lys Arg Lys Val Pro Met Lys Ile His Met
 1               5                  10
```

<210> SEQ ID NO 21
<211> LENGTH: 456
<212> TYPE: DNA
<213> ORGANISM: Artificial Sequence
<220> FEATURE:
<223> OTHER INFORMATION: Description of Artificial Sequence: DNA
    encoding carboxy terminal fusion of a portion of the maize HRGP
    to GFPm
<221> NAME/KEY: CDS
<222> LOCATION: (1)..(456)

<400> SEQUENCE: 21

```
tac act cca agc cct aag cca ccg gct acc aag cct ccc acg ccc aag      48
Tyr Thr Pro Ser Pro Lys Pro Pro Ala Thr Lys Pro Pro Thr Pro Lys
  1               5                  10                  15 ccg acc ccg cca acg tac acc cct tcg cca aag cct ccg aca ccc aag      96
Pro Thr Pro Pro Thr Tyr Thr Pro Ser Pro Lys Pro Pro Thr Pro Lys
             20                  25                  30 ccg acc ccg ccg acg tac acc cct tct ccc aag cct ccg acg ccc aag     144
Pro Thr Pro Pro Thr Tyr Thr Pro Ser Pro Lys Pro Pro Thr Pro Lys
         35                  40                  45 ccg acc ccg ccg acg tac act cca agc ccc aag cct ccc aca cac ccg     192
Pro Thr Pro Pro Thr Tyr Thr Pro Ser Pro Lys Pro Pro Thr His Pro
     50                  55                  60 acg ccc aag ccg acc cca ccg acg tac acc cct tcc cca aag cct ccg     240
Thr Pro Lys Pro Thr Pro Pro Thr Tyr Thr Pro Ser Pro Lys Pro Pro
 65                  70                  75                  80 acg ccc aag ccg acc cca ccg acg tac acc cct tcc cca aag cct ccg     288
Thr Pro Lys Pro Thr Pro Pro Thr Tyr Thr Pro Ser Pro Lys Pro Pro
                 85                  90                  95 aca ccc aag ccg acc cca ccg acg tac acc cct tcc cca aag cct ccg     336
Thr Pro Lys Pro Thr Pro Pro Thr Tyr Thr Pro Ser Pro Lys Pro Pro
            100                 105                 110 aca ccc aag ccg acc cca ccg acg tac act ccc aca ccg aag ccg ccg     384
Thr Pro Lys Pro Thr Pro Pro Thr Tyr Thr Pro Thr Pro Lys Pro Pro
        115                 120                 125 gcc acc aag ccg ccc acc tac act ccg acg ccg ccg gtg tct cac acc     432
Ala Thr Lys Pro Pro Thr Tyr Thr Pro Thr Pro Pro Val Ser His Thr
    130                 135                 140 ccc agc ccg ccg cca cca tac tac                                     456
Pro Ser Pro Pro Pro Pro Tyr Tyr
145                 150
```

<210> SEQ ID NO 22
<211> LENGTH: 152
<212> TYPE: PRT
<213> ORGANISM: Artificial Sequence
<220> FEATURE:
<223> OTHER INFORMATION: Description of Artificial Sequence: Carboxy
    terminal fusion of a portion of the maize HRGP to GFPm

<400> SEQUENCE: 22

```
Tyr Thr Pro Ser Pro Lys Pro Pro Ala Thr Lys Pro Pro Thr Pro Lys
  1               5                  10                  15

Pro Thr Pro Pro Thr Tyr Thr Pro Ser Pro Lys Pro Pro Thr Pro Lys
             20                  25                  30

Pro Thr Pro Pro Thr Tyr Thr Pro Ser Pro Lys Pro Pro Thr Pro Lys
         35                  40                  45

Pro Thr Pro Pro Thr Tyr Thr Pro Ser Pro Lys Pro Pro Thr His Pro
     50                  55                  60

Thr Pro Lys Pro Thr Pro Pro Thr Tyr Thr Pro Ser Pro Lys Pro Pro
```

| | | | | | | 65 | | | | 70 | | | | 75 | | | | 80 | |
|---|---|---|---|---|---|---|---|---|---|---|---|---|---|---|---|---|---|---|---|

Thr Pro Lys Pro Thr Pro Pro Thr Tyr Thr Pro Ser Pro Lys Pro Pro
                               85                   90                 95

Thr Pro Lys Pro Thr Pro Pro Thr Tyr Thr Pro Ser Pro Lys Pro Pro
                100                    105               110

Thr Pro Lys Pro Thr Pro Pro Thr Tyr Thr Pro Thr Pro Lys Pro Pro
           115                  120               125

Ala Thr Lys Pro Pro Thr Tyr Thr Pro Thr Pro Val Ser His Thr
    130                135               140

Pro Ser Pro Pro Pro Tyr Tyr
145           150

<210> SEQ ID NO 23
<211> LENGTH: 621
<212> TYPE: DNA
<213> ORGANISM: Artificial Sequence
<220> FEATURE:
<221> NAME/KEY: CDS
<222> LOCATION: (1)..(621)
<223> OTHER INFORMATION: Description of Artificial Sequence: Superoxide
     dismutase coding sequence fused to GFPm

<400> SEQUENCE: 23

```
gtg gct gag tac acg ctg ccg gat ctg gat tac gac tac agc gcc ctg      48
Val Ala Glu Tyr Thr Leu Pro Asp Leu Asp Tyr Asp Tyr Ser Ala Leu
 1               5                  10                  15 gaa ccc cac atc tcc ggg cag atc aac gag ctg cac cat tcc aag cac      96
Glu Pro His Ile Ser Gly Gln Ile Asn Glu Leu His His Ser Lys His
             20                  25                  30 cac gcc gcc tac gtc gcc ggt gcc aac acg gca ctg gag aag ctg gaa     144
His Ala Ala Tyr Val Ala Gly Ala Asn Thr Ala Leu Glu Lys Leu Glu
         35                  40                  45 gcc gcc cgt gag gcc ggc gat cac agc gcg atc ttc ctg cac gag aag     192
Ala Ala Arg Glu Ala Gly Asp His Ser Ala Ile Phe Leu His Glu Lys
     50                  55                  60 aac ctc gcg ttc cac ctc ggc gga cac gtc aac cac tcc atc tgg tgg     240
Asn Leu Ala Phe His Leu Gly Gly His Val Asn His Ser Ile Trp Trp
 65                  70                  75                  80 aag aac ctg tcc ccc aac ggt ggc gac aag ccg gtc ggc gag ctg gcc     288
Lys Asn Leu Ser Pro Asn Gly Gly Asp Lys Pro Val Gly Glu Leu Ala
                 85                  90                  95 gcg gcc atc gac gac cag ttc ggt tcg ttc gac aag ttc cgc gcg cag     336
Ala Ala Ile Asp Asp Gln Phe Gly Ser Phe Asp Lys Phe Arg Ala Gln
            100                 105                 110 ttc acc gcc gcg gcc aac ggc ctg cag ggc tcg ggc tgg gcg gtg ctc     384
Phe Thr Ala Ala Ala Asn Gly Leu Gln Gly Ser Gly Trp Ala Val Leu
        115                 120                 125 ggt tac gac acc ctc ggc cag aag ctg ctg acc ttc cag ctc tac gac     432
Gly Tyr Asp Thr Leu Gly Gln Lys Leu Leu Thr Phe Gln Leu Tyr Asp
    130                 135                 140 cag cag gcc aac gtg ccg ctg ggc atc atc ccg ctg ctc cag gtc gac     480
Gln Gln Ala Asn Val Pro Leu Gly Ile Ile Pro Leu Leu Gln Val Asp
145                 150                 155                 160 atg tgg gag cac gcc ttc tac ctg cag tac aag aac gtc aag gcc gac     528
Met Trp Glu His Ala Phe Tyr Leu Gln Tyr Lys Asn Val Lys Ala Asp
                165                 170                 175 tac gtg acc gcg ttc tgg aac gtc gtc aac tgg gcc gac gtg cag gac     576
Tyr Val Thr Ala Phe Trp Asn Val Val Asn Trp Ala Asp Val Gln Asp
            180                 185                 190 cgc ttc ggc aag gcc gtc aac cag ggc aag ggc ctt atc ttc ggg         621
Arg Phe Gly Lys Ala Val Asn Gln Gly Lys Gly Leu Ile Phe Gly
        195                 200                 205
```

-continued

```
Arg Phe Gly Lys Ala Val Asn Gln Gly Lys Gly Leu Ile Phe Gly
        195                 200                 205

<210> SEQ ID NO 24
<211> LENGTH: 207
<212> TYPE: PRT
<213> ORGANISM: Artificial Sequence
<220> FEATURE:
<223> OTHER INFORMATION: Description of Artificial Sequence: Superoxide
      dismutase fused to GFPm

<400> SEQUENCE: 24

Val Ala Glu Tyr Thr Leu Pro Asp Leu Asp Tyr Asp Tyr Ser Ala Leu
 1               5                  10                  15

Glu Pro His Ile Ser Gly Gln Ile Asn Glu Leu His His Ser Lys His
            20                  25                  30

His Ala Ala Tyr Val Ala Gly Ala Asn Thr Ala Leu Glu Lys Leu Glu
        35                  40                  45

Ala Ala Arg Glu Ala Gly Asp His Ser Ala Ile Phe Leu His Glu Lys
    50                  55                  60

Asn Leu Ala Phe His Leu Gly Gly His Val Asn His Ser Ile Trp Trp
 65                 70                  75                  80

Lys Asn Leu Ser Pro Asn Gly Gly Asp Lys Pro Val Gly Glu Leu Ala
                85                  90                  95

Ala Ala Ile Asp Asp Gln Phe Gly Ser Phe Asp Lys Phe Arg Ala Gln
            100                 105                 110

Phe Thr Ala Ala Ala Asn Gly Leu Gln Gly Ser Gly Trp Ala Val Leu
        115                 120                 125

Gly Tyr Asp Thr Leu Gly Gln Lys Leu Leu Thr Phe Gln Leu Tyr Asp
    130                 135                 140

Gln Gln Ala Asn Val Pro Leu Gly Ile Ile Pro Leu Leu Gln Val Asp
145                 150                 155                 160

Met Trp Glu His Ala Phe Tyr Leu Gln Tyr Lys Asn Val Lys Ala Asp
                165                 170                 175

Tyr Val Thr Ala Phe Trp Asn Val Val Asn Trp Ala Asp Val Gln Asp
            180                 185                 190

Arg Phe Gly Lys Ala Val Asn Gln Gly Lys Gly Leu Ile Phe Gly
        195                 200                 205
```

What is claimed is:

1. An isolated DNA molecule comprising a nucleotide sequence selected from the group consisting of:
   (a) SEQ ID NO: 1 (GFPm)
   (b) SEQ ID No:1, wherein the nucleotides TCC at positions 193–195 are changed to ACG (GFPr);
   (c) SEQ ID NO: 1, wherein nucleotides TAC at positions 196–198 are changed to CAC (BFP); and
   (d) SEQ ID NO: 1, wherein nucleotides TTC at positions 295–297 are changed to AGC, nucleotides ATG at positions 457–459 are changed to ACC, and nucleotides GTG at positions 487–489 are changed to GCC (GFPs).

2. An isolated DNA molecule according to claim 1, wherein said isolated DNA molecule is operably linked to a nucleotide sequence encoding a signal sequence for subcellular localization which directs the protein encoded by said DNA molecule to a subcellular compartment.

3. An expression vector comprising said DNA molecule of claim 1.

4. The expression vector according to claim 3, wherein said DNA molecule is operably linked to a nucleotide sequence encoding a signal sequence which directs the protein encoded by said DNA molecule to a subcellular compartment.

5. A method of using said expression vector of claim 3 to produce a transformed plant, comprising the steps of introducing said expression vector into regenerable plant cells, screening for transformed cells containing said GFPm, GFPr, BFP, or GFPs, and regenerating a transformed plant from said transformed cells identified by said screening as containing GFPm, GFPr, BFP, or GFPs.

6. The method of claim 5, wherein said regenerable plant cells are selected from the group consisting of Zea, Brassica and Helianthus cells.

7. A transgenic plant containing said DNA molecule of claim 1.

8. A transgenic plant containing said DNA molecule of claim 1, wherein said plant is selected from the group consisting of the genera Zea, Brassica, and Helianthus.

9. A transgenic Zea mays plant containing said DNA molecule of claim 1.

10. The expression vector according to claim 3, wherein said DNA molecule is operably linked to a first promoter and the expression vector optionally comprises a second promoter linked to a foreign gene.

11. The expression vector of claim 10, wherein the first promoter is an inducible, constitutive or tissue-specific promoter.

12. The expression vector of claim 11, wherein the first promoter is an estrogen-inducible promoter, an estradiol-inducible promoter, the ACE1 promoter, the IN2 promoter or the tetracycline repressor promoter.

13. The expression vector of claim 11, wherein the first promoter is a CaMV, actin, ubiquitin, pEMU, MAS or histone promoter.

14. The expression vector of claim 3, further comprising a nucleotide sequence for subcellular localization which directs said DNA to a subcellular compartment.

15. The expression vector of claim 14, wherein the subcellular localization sequence directs expression to the mitochondria, cytoplasm, peroxisome, endoplasmic reticulum, cell wall, apoplast or nucleus.

16. The expression vector of claim 15, wherein the promoter is a mitochondrial promoter and said subcellular localization sequence directs expression to the mitochondria.

17. A transgenic plant cell comprising the expression vector of claim 10.

18. The plant cell of claim 17 wherein the plant cell is produced without negative selection.

19. A transgenic regenerated from the plant cell of claim 17.

20. The plant of claim 19, wherein the plant is a monocot or a dicot.

21. The plant of claim 20, wherein the monocot is of the genera Zea.

22. The plant of claim 20, wherein the dicot is of the genera Brassica or Helianthus.

23. A transgenic seed of the plant of claim 20.

24. The expression vector of claim 10, further comprising a recombinase-specific target sequence wherein the target sequence flanks the 5-prime and 3-prime ends of the first promoter, the DNA molecule or both.

25. The expression vector of claim 24, wherein the recombinase-specific target sequence comprises FLP/FRT, Ac/DS or cre/lox.

26. A transgenic plant cell comprising the expression vector of claim 24.

27. A transgenic plant regenerated from the plant cell of claim 26.

28. The plant of claim 27, wherein the plant is a monocot or a dicot.

29. The plant of claim 28, wherein the monocot is of the genera Zea.

30. The plant of claim 29, wherein the dicot is of the genera Brassica or Helianthus.

31. A transgenic seed of the plant of claim 30.

32. A method for producing a transgenic plant, comprising the steps:
  (a) constructing at least one expression vector comprising (i) a first promoter, operably linked to the isolated DNA molecule of claim 1, and (ii) a second promoter operably linked to a foreign gene;
  (b) introducing said expression vector into regenerable plant cells;
  (c) screening for transformed plant cells containing said green fluorescent protein; and
  (d) regenerating transformed plants from transformed plant cells identified by said screening.

33. The expression vector of claim 14, wherein the subcellular localization sequence directs expression to the chloroplast.

* * * * *